United States Patent
Gingras et al.

(10) Patent No.: US 9,937,282 B2
(45) Date of Patent: Apr. 10, 2018

(54) MEDICAL DEVICE

(75) Inventors: Peter Gingras, Galway (IE); Dean King, Galway (IE)

(73) Assignee: Proxy Biomedical Limited (IE)

( * ) Notice: Subject to any disclaimer, the term of this patent is extended or adjusted under 35 U.S.C. 154(b) by 227 days.

(21) Appl. No.: 12/911,193

(22) Filed: Oct. 25, 2010

(65) Prior Publication Data

US 2011/0082481 A1    Apr. 7, 2011

Related U.S. Application Data

(63) Continuation of application No. 11/093,983, filed on Mar. 30, 2005, now abandoned.

(60) Provisional application No. 60/642,607, filed on Jan. 10, 2005, provisional application No. 60/558,067, filed on Mar. 30, 2004.

(51) Int. Cl.
| | |
|---|---|
| *A61F 2/02* | (2006.01) |
| *A61L 27/56* | (2006.01) |
| *A61L 27/50* | (2006.01) |
| *D04B 21/12* | (2006.01) |
| *A61F 2/00* | (2006.01) |

(52) U.S. Cl.
CPC ............ *A61L 27/56* (2013.01); *A61F 2/0063* (2013.01); *A61L 27/50* (2013.01); *D04B 21/12* (2013.01); *A61F 2/0045* (2013.01); *A61F 2002/0068* (2013.01); *D10B 2509/08* (2013.01); *Y10T 442/30* (2015.04); *Y10T 442/40* (2015.04)

(58) Field of Classification Search
CPC .................. A61F 2/0063; A61F 2/0045; A61F 2002/0068; A61L 27/50; A61L 27/56; D04B 21/12; D10B 2509/08; Y10T 442/30; Y10T 442/40

USPC ............ 606/151; 623/23.72–23.76; 424/422, 424/423, 424, 443; 442/50, 304, 308, 442/309, 397
See application file for complete search history.

(56) References Cited

U.S. PATENT DOCUMENTS

| | | | |
|---|---|---|---|
| 2,671,444 A |   | 3/1954 | Pease, Jr. |
| 2,764,976 A | * | 10/1956 | Skiles, Jr. et al. .............. 602/51 |
| 3,054,406 A |   | 9/1962 | Usher |
| 3,124,136 A | * | 3/1964 | Usher .......................... 606/213 |
| 3,479,670 A |   | 11/1969 | Medell |

(Continued)

FOREIGN PATENT DOCUMENTS

| | | |
|---|---|---|
| WO | WO 02/26108 | 4/2002 |
| WO | WO 02/39890 | 5/2002 |
| WO | WO 04/017862 | 3/2004 |

OTHER PUBLICATIONS

Kling et al., "Modified Mesh for Hernia Repair that is Adapted to the Physiology of the Abdominal Wall," Eur. J. Surg. 164:951-960, 1998.

(Continued)

*Primary Examiner* — Jing Ou
(74) *Attorney, Agent, or Firm* — Tarolli, Sundheim, Covell & Tummino LLP

(57) ABSTRACT

A soft tissue implant comprises a condensed surgical mesh having a plurality of monofilament biocompatible fibers 12. Condensing of the fibers reduces the void space between adjacent fibers 12 in the mesh and reduces the surface area of the fibers 12 available for contact with tissue. Condensation of the fibers 12 may be achieved by applying mechanical pressure, and/or vacuum, and/or heat to the mesh.

31 Claims, 27 Drawing Sheets

(56) References Cited

U.S. PATENT DOCUMENTS

| | | | |
|---|---|---|---|
| 3,485,706 A * | 12/1969 | Evans | D04H 1/495 |
| | | | 162/115 |
| 3,573,164 A * | 3/1971 | Friedberg et al. | D21F 1/0027 |
| | | | 139/383 A |
| 4,107,364 A * | 8/1978 | Sisson | D04H 3/16 |
| | | | 428/152 |
| 4,347,847 A | 9/1982 | Usher | |
| 4,452,245 A | 6/1984 | Usher | |
| 4,633,873 A | 1/1987 | Dumincan et al. | |
| 4,693,720 A | 9/1987 | Scharnberg et al. | |
| 4,815,499 A * | 3/1989 | Johnson | D21F 1/0045 |
| | | | 139/383 A |
| 4,838,884 A | 6/1989 | Dumican et al. | |
| 4,857,041 A | 8/1989 | Annis et al. | |
| 5,112,344 A | 5/1992 | Petros | |
| 5,292,328 A | 3/1994 | Hain et al. | |
| 5,459,912 A * | 10/1995 | Oathout | B32B 5/26 |
| | | | 28/104 |
| 5,569,273 A | 10/1996 | Titone et al. | |
| 5,611,515 A | 3/1997 | Benderev et al. | |
| 5,637,074 A | 6/1997 | Andino et al. | |
| 5,840,011 A | 11/1998 | Landgrebe et al. | |
| 5,842,478 A | 12/1998 | Benderev et al. | |
| 5,860,425 A | 1/1999 | Benderev et al. | |
| 5,899,909 A | 5/1999 | Benderev et al. | |
| 6,039,686 A | 3/2000 | Kovac | |
| 6,042,534 A | 3/2000 | Gellman et al. | |
| 6,042,592 A | 3/2000 | Schmitt | |
| 6,042,593 A | 3/2000 | Storz et al. | |
| 6,090,116 A | 7/2000 | D'Aversa | |
| 6,110,101 A | 8/2000 | Tihon | |
| 6,258,124 B1 | 7/2001 | Darois et al. | |
| 6,270,530 B1 | 8/2001 | Eldridge et al. | |
| 6,273,852 B1 | 8/2001 | Lehe et al. | |
| 6,287,316 B1 | 9/2001 | Agarwal et al. | |
| 6,306,079 B1 | 10/2001 | Trabucco | |
| 6,319,264 B1 | 11/2001 | Tormala et al. | |
| 6,355,065 B1 | 3/2002 | Gabbay | |
| 6,375,662 B1 | 4/2002 | Schmitt | |
| 6,406,423 B1 | 6/2002 | Scetbon | |
| 6,408,656 B1 | 6/2002 | Ory et al. | |
| 6,478,727 B2 | 11/2002 | Scetbon | |
| 6,638,284 B1 | 10/2003 | Rousseau et al. | |
| 6,702,827 B1 | 3/2004 | Lund et al. | |
| 2002/0083820 A1 | 7/2002 | Greenhalgh | |
| 2002/0123750 A1 * | 9/2002 | Eisermann et al. | 606/69 |
| 2002/0138025 A1 * | 9/2002 | Gellman et al. | 602/4 |

OTHER PUBLICATIONS

Junge et al., "Elasticity of the Anterior Abdominal Wall and Impact for Reparation of Incisional Hernias Using Mesh Implants," Hernia 5:113-118, 2001.

Welty et al., "Functional Impairment and Complaints Following Incisional Hernia Repair with Different Polypropylene Meshes," Hernia 5:142-147, 2001.

Klinge et al., "Foreign Body Reaction to Meshes Used for the Repair of Abdominal Wall Hernias," Eur. J. Surg. 165:665-673, 1999.

Chu et al., "Characterization of Morphologic and Mechanical Properties of Surgical Mesh Fabrics," J. Bio. Mat. Res. 19:903-916, 1985.

European Notice of Allowance; Application No. 05718825.2-2107; dated Jul. 20, 2010; Applicant: Proxy Biomedical Limited; 4 pages.

European Office Action; Application No. 05718825.2-2107; dated Sep. 14, 2009; Applicant: Proxy Biomedical Limited; 5 pages.

European Office Action; Application No. 05718825.2-2107; dated Dec. 10, 2008; Applicant: Proxy Biomedical Limited; 3 pages.

European Office Action; Application No. 05718825.2-2107; dated Jul. 19, 2007; Applicant: Proxy Biomedical Limited; 2 pages.

International Search Report and Written Opinion; Application No. PCT/IE2005/000035; dated Jun. 16, 2005; 9 pages.

* cited by examiner

MEDICAL DEVICE

This application is a continuation of U.S. application Ser. No. 11/093,983, filed on Mar. 30, 2005, now abandoned, which claims the benefit of U.S. Application Nos. 60/558,067, filed on Mar. 30, 2004 and 60/642,607, filed on Jan. 10, 2005, each of which are incorporated herein by reference in their entirety.

FIELD OF THE INVENTION

This invention relates generally to medical devices and more specifically to soft tissue implants that can be used to repair injured or otherwise defective tissue within the body (e.g., pelvic floor prolapse and hernias).

BACKGROUND

Stress urinary incontinence (SUI), pelvic floor prolapse, and hernias are serious health concerns worldwide. Millions of people suffer from these problems, and surgical procedures involving the placement of implants to stabilize or support the affected tissue are required.

Devices for treating tissue defects can be constructed from synthetic materials such as polypropylene, polytetrafluoroethylene, polyester, and silicone. Devices constructed from non-synthetic materials can include allografts, homografts, heterografts, xenografts, autologous tissues, cadaveric fascia, and fascia lata. The supply of non-synthetic devices can vary greatly and certain sizes of non-synthetic materials can be difficult to obtain. For example, autologous material may be difficult or impossible to harvest from some patients due to the health of the patient or the size of the tissue needed for a repair.

Biomaterials, which work either by mechanical closure or by inducing strong scar tissue, can also be used. However, the synthetic material can increase the rate of local wound complications such as seromas (by about 30-50%), paraesthesia (by about 10-20%), and restriction of mobility (by about 25%) (see Klinge et al., *Eur. J. Surg.* 164:951-960, 1998). More specifically, biomaterial implants are used to support the abdominal wall, which has an average displacement elasticity of 25% at a maximum tensile strength of 16 N/cm (see Junge et al., *Hernia* 5:113-118, 2001). Biomaterials with initially low bending stiffness may turn into hard sheets in the post implant period and fail to exhibit 25% strain under forces of 16 N/cm. With excessive scar tissue formation, there is a decrease in abdominal wall mobility. Histological analysis of explanted biomaterials has revealed persistent inflammation at the interface, even after several years of implantation, which is influenced by the weight of the biomaterial and the surface area in contact with the recipient tissue. The persistent foreign body reaction is independent of the inflammation time, but considerably affected by the type of biomaterial (see Welty et al., *Hernia* 5:142-147, 2001; and Klinge et al., *Eur. J Surg.* 165:665-673, 1999). Consequently, the persistence of a foreign body reaction at the biomaterial-tissue interface might cause severe problems, particularly in young patients, in whom the biomaterial is expected to hold for prolonged periods of time.

Bard Mesh™ is a non-absorbable implant that is made from monofilament polypropylene fibres using a knitting process (C.R. Bard, Inc., Cranston, R.I.; see also U.S. Pat. No. 3,054,406; U.S. Pat. No. 3,124,136; and Chu et al., *J. Bio. Mat. Res.* 19:903-916, 1985). The thickness for Bard Mesh™ and other commercially available implants is provided in the table below. As indicated, the thinnest of these materials has a thickness of 0.016 inches.

| Material | Company | Code No. | Thickness (inches) |
| --- | --- | --- | --- |
| Bard Mesh | C. R. Bard/Davol | 112660 | 0.026 |
| Prolene Mesh | J&J/Ethicon | PML | 0.020 |
| Prolene Soft Mesh | J&J/Ethicon | SPMXXL | 0.016 |
| Gore-Tex Soft Tissue Patch | W. L. Gore | 1315020020 | 0.079 |
| ProLite | Atrium Medical | 1001212-00 | 0.019 |
| ProLite Ultra | Atrium Medical | 30721 | 0.016 |

Additional non-absorbable meshes are known (see U.S. Pat. Nos. 2,671,444; 4,347,847; 4,452,245; 5,292,328; 5,569,273; 6,042,593; 6,090,116; 6,287,316 (this patent describes the mesh marketed as Prolene™; and U.S. Pat. No. 6,408,656). These products are all made using synthetic fibre technology. Different knit patterns impart unique mechanical properties to each configuration.

A variety of absorbable or partially absorbable materials have been described (see U.S. Pat. Nos. 4,633,873; 4,693,720; 4,838,884; and 6,319,264). There are also a variety of implants used to treat urinary incontinence in women (see U.S. Pat. Nos. 4,857,041; 5,840,011; 6,042,534; 6,110,101; 6,306,079; and 6,355,065; see also U.S. Pat. Nos. 5,112,344; 5,611,515; 5,637,074; 5,842,478; 5,860,425; 5,899,909; 6,039,686; 6,273,852; 6,406,423; 6,478,727; 6,702,827; WO 2004/017862; WO 02/39890; and WO 02/26108).

At present, monofilament polypropylene surgical meshes are the most widely used soft tissue implants. Although serious complications associated with implants are infrequent, they are well documented. Moreover, each of the implants presently in use are believed to have one or more deficiencies. For example, their construction can result in characteristics (e.g., wall thickness and surface area) that increase the risk of an inflammatory response or of infection; seromas can form postoperatively within the space between the prosthesis and the host tissues; due to material content, width, and wall thickness, surgeons must make large incisions for implantation (the present implants can be difficult to deploy in less invasive surgical methods); rough and irregular implant surfaces can irritate tissues and lead to the erosion of adjacent tissue structures; adhesions to the bowel can form when the implant comes in direct contact with the intestinal tract; where pore size is reduced, there can be inadequate tissue ingrowth and incorporation; and the pore size and configuration of the implants does not permit adequate visualization through the implant during laparoscopic procedures. Additional complications include pain, discomfort, obstruction, and organ perforations.

SUMMARY

The present invention features medical devices that include biocompatible material for stabilising or supporting a tissue of a patient's body. Methods for making the devices are also within the scope of the invention. More specifically, the devices include condensed surgical meshes with reduced void and surface contact areas (e.g., a condensed monofilament surgical mesh) produced from a biocompatible polymer without added materials (e.g. coatings). The studies conducted with the condensed mesh indicate that, by reducing the void space therein (e.g., the space between fibres within the mesh), the mesh is less likely to cause inflammation. With a reduced surface area, there are fewer places for inflammatory cells to aggregate. Void area reduction may create a superior device in other ways as well.

The term "implant" may be used instead of "device." Soft tissue implants are those suitable for application to any soft tissue within a patient's body, and they may also be referred to as surgical implants. While the patient may be a human, the invention is not so limited; the implants can be used to repair or stabilize soft tissue in any animal.

The methods of the invention include methods of making a soft tissue implant by providing a surgical mesh and condensing the surgical mesh to generate material useful as a soft tissue implant. If desired, one can further alter the size or shape of the material (e.g., one can trim the implant or fold or roll it into a conical or tubular shape). As with other medical devices, the implants may be sterilized before use.

The surgical mesh can be obtained from a commercial supplier or made using methods known in the art. For example, a mesh can be made by extruding a biocompatible polymer or copolymer into a fibre and knitting or weaving the fibres together. To facilitate production, the process can be mechanized. For example, the knitted mesh of the invention can be made on any two-bar warp loom.

Useful polymers and copolymers are described as biocompatible as they are non-toxic or sufficiently harmless to allow their use in human patients. The polymers and copolymers can be non-absorbable (e.g., they may made with polypropylene, polyethylene, polyethylene terephthalate, polytetrafluoroethylene, polyaryletherketone, nylon, fluorinated ethylene propylene, polybutester, or silicone) or absorbable (polyglycolic acid (PGA), polylactic acid (PLA), polycaprolactone, polydioxanone or polyhydroxyalkanoate, or a copolymer thereof. Absorbable implants degrade following implantation, and the rate of degradation can vary greatly depending upon the amount and type of material used. In other embodiments, the polymer or copolymer can include a naturally occurring biological molecule, or a variant thereof, such as collagen. The fibres can be intertwined in many different ways by knitting or weaving. The spaces within the mesh may be referred to as cells or pores, and a given mesh can include uniformly or non-uniformly patterned cells having any number of shapes (e.g., the cells or pores can be substantially round, square, oval-shaped or diamond-shaped). The size of the pores can also vary and may be uniform or non-uniform. For example, the mesh can include pores that are about 50 μm in diameter.

The mesh can be condensed in any way that reduces the void space between the fibres. For example, one can apply mechanical pressure, vacuum, and/or heat to the mesh. The fibres are thermally set to a desired shape that reduces the void space between and around the fibres of the surgical mesh. The condensation force is applied for a time and under conditions sufficient to reduce the void space within the mesh or the area of the implant available to contact a patient's tissue. We may refer to that area as the surface contact area.

The fibres most useful for creating the implant are monofilament fibres. Monofilament fibres are less prone to infection and inflammation. Consequently, a surgical mesh constructed from monofilament fibres is a preferred structure compared to multifilament based surgical meshes. Monofilament fibres have a consistent cross sectional area compared to multifilament fibres that have small individual fibres bundled together. Multifilament fibres have an increased surface contact area compared to monofilament fibres of the same diameter. In addition, monofilament fibres are more stable when subjected to condensation treatment and are less likely to move in relation to adjacent fibres which preserves the condensed structure.

The compressive force can be applied to the mesh uniformly, in which case the void space will be reduced in a substantially uniform way within the entire mesh. Alternatively, the force (e.g., pressure) can be applied to the mesh non-uniformly. In that event, the extent to which the void space is reduced will vary from one region of the mesh to another (the reduction being greater where the force is greater). To facilitate condensation, the force can be applied to the mesh while the mesh is under vacuum.

Either before or after condensation, the mesh can be altered. For example, the mesh can be cut or otherwise fashioned into a different shape before condensation. The shape change can include inserting, into the mesh or material condensed therefrom, an opening for receiving an attachment element (e.g., a suture, staple, or other fixation device). The force may be applied to the mesh in such a way that a region for receiving an attachment element (e.g., a point along the edge, or a folded edge, of the mesh or material) varies in density from a region that is not intended to receive an attachment element.

Depending upon the strength of the condensation, the thickness (or average thickness) of the material can vary. For example, the material can be about 0.001-0.040 inches thick. The overall dimensions of the mesh or material can be unique or can be those of any presently available surgical mesh or implant. For example, the condensed materials described herein can be fashioned to support tissue (e.g., a part of the bladder, urethra, pelvic floor, or abdominal wall) and may have the overall shape of any device presently used to do so.

The invention also features devices (e.g., soft tissue implants) made by any of the methods described herein. These devices are described further below and illustrated in the drawings.

In specific embodiments, the methods of the invention include providing a surgical mesh; placing the surgical mesh under vacuum; heating the surgical mesh; compressing the surgical mesh by applying pressure to the mesh (for a time and under conditions sufficient to reduce the void space within the mesh or the surface contact area); and cleaning and/or sterilizing the mesh, thereby generating material useful as a soft tissue implant. The heating process can impact longitudinal elasticity; applying heat while applying tension to the implant can reduce elasticity).

In specific embodiments, the invention features a soft tissue implant comprising a woven or knit monofilament mesh having a density greater than 0.081 g/cm$^3$, the space between the monofilament mesh constituting pores of about 500 μm to about 10 mm in diameter.

The implants of the present invention offer a combination of high porosity, high strength, and low material content, and they may have one or more of the following advantages. They can include pores or porous structures that stimulate fibrosis and reduce inflammation; they can reduce the risk of erosion and formation of adhesions with adjacent tissue (this is especially true with implants having a smooth surface and reduced surface contact area) and atraumatic (e.g., smooth, tapered, or rounded edges); they can simulate the physical properties (e.g. elasticity) of the tissue being repaired or replaced, which is expected to promote more complete healing and minimise patient discomfort; their surface areas can be reduced relative to prior art devices (having a reduced amount of material in contact with tissue may decrease the likelihood of an immune or inflammatory response). Practically, the techniques that can be used to produce the implants of the present invention are efficient and reproducible. The implants described herein should provide enhanced biocompatibility in a low profile configuration while maintaining the requisite strength for the intended purpose. The implants may also have improved wrinkle recovery memory.

According to the invention there is provided a soft tissue implant comprising a condensed surgical mesh, the mesh comprising one or more biocompatible fibres, at least one of the fibres comprising a monofilament fibre.

In one embodiment of the invention each fibre in the mesh comprises a monofilament fibre. The mesh may be knit from one or more fibres. The mesh may be woven from one or more fibres.

In one embodiment along at least part of at least one fibre, the fibre is condensed. The mesh may have a void space between adjacent fibres in the mesh, and along the condensed part of the fibre, the mesh void space is reduced. The distance between adjacent fibres in the mesh may be in the range of from approximately 5 μm to approximately 500 μm. Along the condensed part of the fibre:

$$\frac{A_v}{A_F} \text{ may be} \leq 1.5$$

where:
 $A_v$=area of the void between adjacent fibres in the mesh available for tissue infiltration.
 $A_F$=cross-sectional area of the fibre.
In one case $$\frac{A_v}{A_F} \leq 1.0$$

$\frac{A_v}{A_F}$ may be approximately equal to 0.6.

Along the condensed part of the fibre, the surface area of the fibre available for contact with tissue may be reduced. Along the condensed part of the fibre:

$$\frac{P_{FC}}{P_F} \text{ may be} \leq 0.8$$

where:
 $P_{FC}$=Perimeter of the fibre, at a cross-section of the fibre, which is available for contact with tissue.
 $P_F$=Total perimeter of the fibre, at a cross-section of the fibre.
In one case $$\frac{P_{FC}}{P_F} \leq 0.65$$

$\frac{P_{FC}}{P_F}$ may be approximately equal to 0.5

In another embodiment the fibres are condensed at least some points of intersection between the fibres. The fibres may be at least partially flattened at least some points of intersection between the fibres. At least some of the points of intersection may be stitch loop intersections.

In one case the mesh has at least one overlap region, at which at least one fibre overlaps at least one other fibre, at least one of the fibres being condensed at the overlap region. At the overlap region, the surface of the mesh available for contact with tissue may be less than the sum of the total surface areas of the overlapping fibres. The ratio of the tissue contact area of the mesh to the sum of the total surface areas of the overlapping fibres may be less than or equal to 0.8. At the overlap region, one fibre may be fused with an overlapping fibre. At the overlap region, one fibre may engage with an overlapping fibre. The engagement of one fibre with an overlapping fibre may substantially prevent in-growth of tissue between the overlapping fibres. The overlapping fibres may be condensed together.

In another embodiment the fibre comprises a polymer and/or a copolymer. The polymer and/or copolymer may be absorbable. The polymer and/or copolymer may be non-absorbable.

The fibre may comprise polypropylene.

In another case the mesh is condensed substantially uniformly. The mesh may comprise a condensed region and an uncondensed region. The mesh may comprise at least two regions which are differentially condensed.

In one embodiment the implant is configured for attachment to tissue. The mesh may comprise one or more attachment points. The mesh may be reinforced in the region of the attachment point. The implant may be configured to facilitate coupling of an attachment element to the mesh. In one case the attachment point comprises an attachment opening in the mesh to receive an attachment element, such as a suture, and/or a staple, and/or an adhesive. The mesh may comprise one or more engagement formations for attachment of the mesh to tissue. The engagement formation may comprise a protrusion. The mesh may comprise a plurality of protrusions configured in a wave-like or dimple like pattern.

In one embodiment at least part of the mesh is treated to increase the coefficient of friction of the mesh. At least part of the mesh may have an increased surface roughness.

In another embodiment the mesh is configured to maintain the position of the mesh relative to tissue. The mesh may comprise one or more engagement formations for engaging tissue.

At least a portion of the mesh may be of a composite configuration. The implant may comprise an inelastic element to reinforce the mesh. The inelastic element may comprise one or more fibres. The inelastic element may be woven into the mesh. The inelastic element may be attached to a surface of the mesh.

In another case the thickness of at least part of the mesh is in the range of from 0.001 inches to 0.04 inches. The thickness of the mesh may be substantially constant across the mesh. The thickness of the mesh may vary across the mesh. The density of at least part of the mesh may be greater than 0.081 g/cm$^3$. The density of the mesh may be substantially constant across the mesh. The density of the mesh may vary across the mesh.

In another embodiment the mesh pore size is uniform across the mesh. The mesh pore size may vary across the mesh.

The implant may comprise a three dimensional structure. The three dimensional structure may comprise a conical shape. The three dimensional structure may comprise a cylindrical shape.

In one embodiment at least some of the mechanical properties of the mesh are substantially omnidirectional. The elasticity of the mesh may be substantially omnidirectional.

In another aspect of the invention there is provided a method of forming a surgical mesh, comprising one or more biocompatible fibres, at least one of the fibres comprising a monofilament fibre, the method comprising the step of condensing at least part of the mesh.

In one embodiment the method comprises the steps of:—
providing the one or more biocompatible fibres; and
forming the surgical mesh from the one or more fibres.

Each fibre in the mesh may comprise a monofilament fibre.

In one case the mesh is condensed by applying heat to at least part of the mesh. The mesh may be condensed by applying pressure to at least part of the mesh. The mesh may be condensed by applying a vacuum to at least part of the mesh.

In one case the method comprises the step of heat-setting the mesh. The step of heat-setting may be performed before the step of condensing. The step of heat-setting may be performed after the step of condensing. The step of heat-setting may be performed during the step of condensing.

In another embodiment the method comprises the step of controlling the texture of the mesh. The method may comprise the step of controlling the texture of the external surface of the mesh. The texture may be controlled by arranging the mesh in contact with a control surface before the step of condensing is performed. The method may comprise the step of maintaining the temperature of the control surface substantially stable. The method may comprise the step of maintaining the pressure of the control surface substantially stable.

In one case the method comprises the step of forming the mesh into a three-dimensional structure. The method may comprise the step of treating the mesh to make at least some of the mechanical properties of the mesh substantially omnidirectional. The mesh may be stretched in a first direction while holding the mesh in a second direction perpendicular to the first direction.

In one case the mesh is formed by knitting the one or more fibres, or weaving the one or more fibres.

In another aspect the invention provides a method of making a soft tissue implant, the method comprising:
(a) providing a surgical mesh; and
(b) condensing the surgical mesh to generate material useful as a soft tissue implant The method may comprise altering the size or shape of the material to generate the soft tissue implant. Providing the surgical mesh may comprise extruding a biocompatible polymer or copolymer into a fibre and forming the surgical mesh from the fibre. In one case the biocompatible polymer or copolymer is a non-absorbable polymer or copolymer. The non-absorbable polymer may be a polymer of polypropylene, polyethylene, polyethylene terephthalate, polytetrafluoroethylene, polyaryletherketone, nylon, fluorinated ethylene propylene, polybutester, or silicone, or a copolymer thereof. In another case the biocompatible polymer or copolymer is an absorbable polymer. The absorbable polymer may be a polymer of polyglycolic acid (PGA), polylactic acid (PLA), polycaprolactone, polydioxanone or polyhydroxyalkanoate, or a copolymer thereof. The biocompatible polymer may be collagen or a copolymer comprising collagen.

In one embodiment forming the surgical mesh comprises knitting the fibre. The mesh may comprise pores of a substantially uniform size. The mesh may comprise pores that are greater than 50 micrometers in diameter.

In one case condensing the surgical mesh comprises applying pressure and, optionally, heat to the mesh. The pressure or heat may be applied for a time and under conditions sufficient to reduce the void space within the mesh. The pressure or heat may be applied for a time and under conditions sufficient to reduce the surface area available for contact with a patient's tissue. The pressure or heat may be applied to the mesh uniformly. The pressure or heat may be applied to the mesh non-uniformly. The pressure or heat may be applied to the mesh while the mesh is under vacuum.

In one case the method comprises inserting, into the material, an opening for receiving an attachment element. The material may be about 0.001-0.040 inches thick. The material may be of a size and shape appropriate for stabilizing or supporting the bladder neck, urethra, pelvic floor, or abdominal wall.

In one embodiment the method comprises fashioning the material into a tubular or conical shape.

The invention also provides a soft tissue implant made by the method of the invention.

In a further aspect the invention provides a method of making a soft tissue implant, the method comprising:
(a) providing a surgical mesh;
(b) condensing the surgical mesh by applying pressure and, optionally, heat to the mesh, wherein the pressure and, optionally, the heat, is applied for a time and under conditions sufficient to reduce the void space within the mesh; and
(c) cleaning or sterilizing the mesh, thereby generating material useful as a soft tissue implant.

The invention provides in a further aspect a soft tissue implant comprising a woven or knit monofilament mesh having a density greater than 0.081 g/cm$^3$, the space between the monofilament mesh constituting pores of about 500 μm to about 10 mm in diameter.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2A depicts the round and oval perimeters of monofilament fibres and the fibre cross sections;

FIG. 2B depicts the perimeters and illustrates the area of the mesh available to contact tissue once implanted into a patient also referred to as the area of void for tissue infiltration;

FIG. 3A depicts the altered perimeters and FIG. 3B illustrates the reduced area of the mesh available for tissue contact;

FIGS. 14A and 14C show a non-condensed mesh after implantation for 28 days at 100× and 200×, respectively;

FIGS. 14B and 14D show a mesh condensed at a force of 75 N/cm$^2$, heat application, and vacuum, after implantation for 28 days at 100× and 200×, respectively;

FIGS. 15A and 15C show a non-condensed mesh after implantation for 28 days at 100× and 200×, respectively; and FIGS. 15B and 15D show a mesh condensed at a force of 75 N/cm$^2$, heat application, and vacuum, after implantation for 28 days at 100× and 200×, respectively.

DETAILED DESCRIPTION

Figure 1:
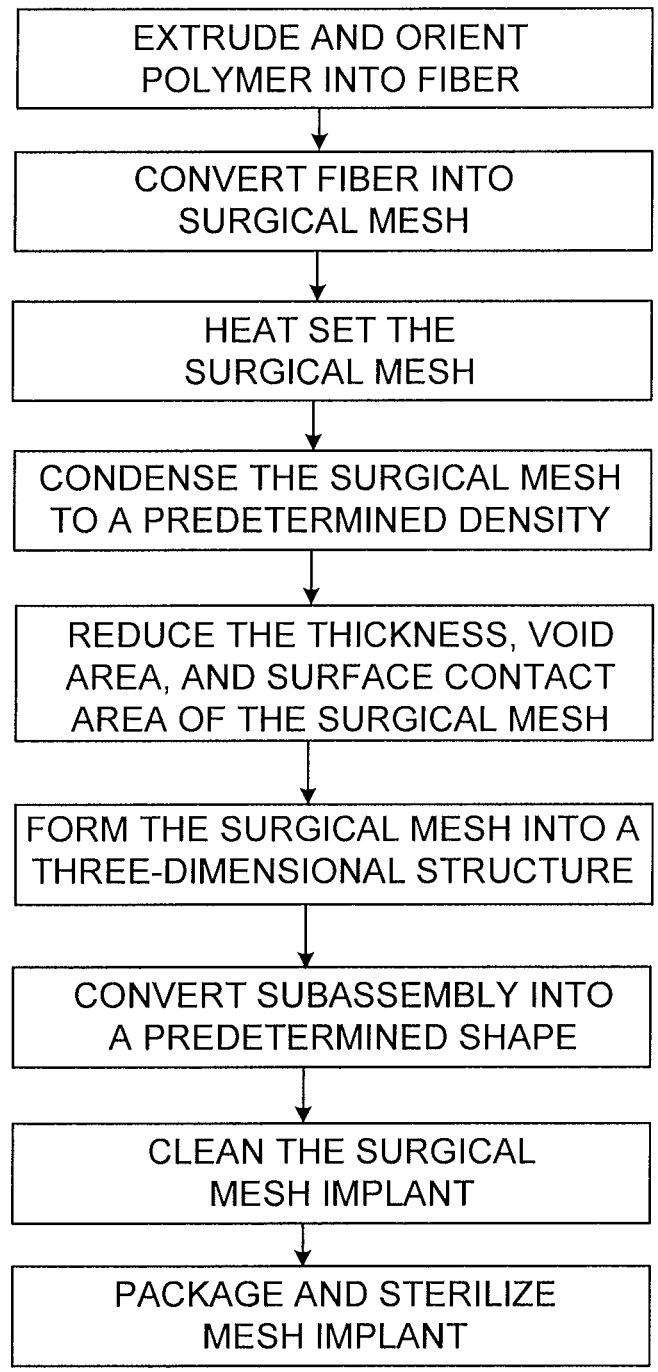
FIG. 1 is a flow chart illustrating some of the steps in a method for producing an implant for treating tissue defects.

Referring to the figures, FIG. 1 illustrates one embodiment of the present methods. While the methods are described further below, they can include the steps of extruding and orienting a polymer into a monofilament fibre; converting the fibre into a surgical mesh; heat setting the surgical mesh; condensing the surgical mesh to a predetermined density; reducing the thickness, void area, and surface contact area of the surgical mesh; forming the surgical mesh into a three-dimensional structure (a subassembly); converting the subassembly into a predetermined shape; cleaning the implant; and packaging and sterilizing the implant.

It will be appreciated that the method described with reference to FIG. 1 is one method according to the invention. However other methods, including only some of the steps described with reference to FIG. 1, also fall within the scope of the invention is suit. It is not essential that all of the steps described with reference to FIG. 1 be included in the method of the invention.

Figure 2A:
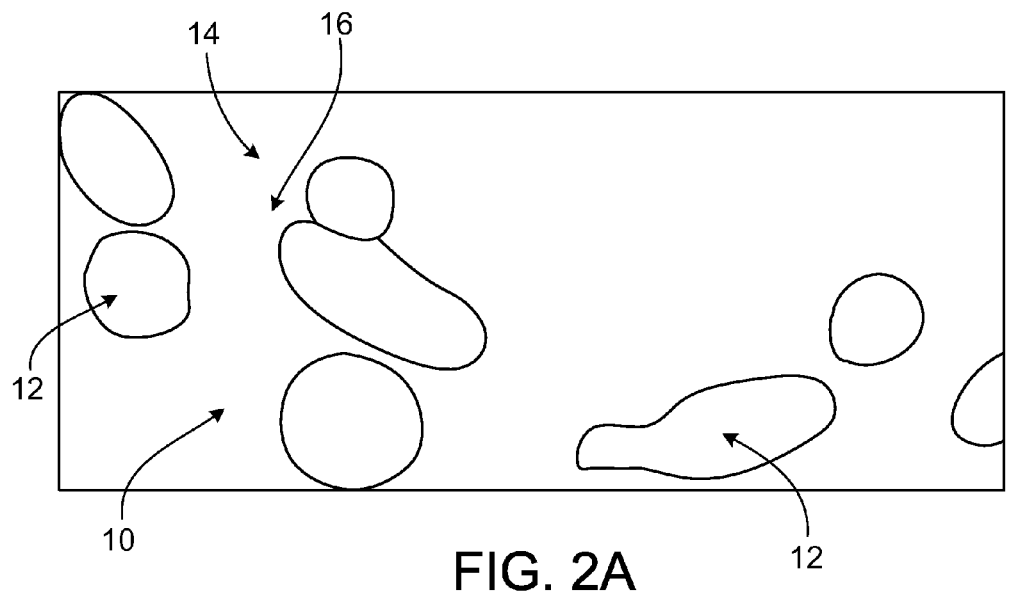
FIGS. 2A and 2B are cross sectional diagrams of an uncondensed surgical mesh implant.
Figure 2B:
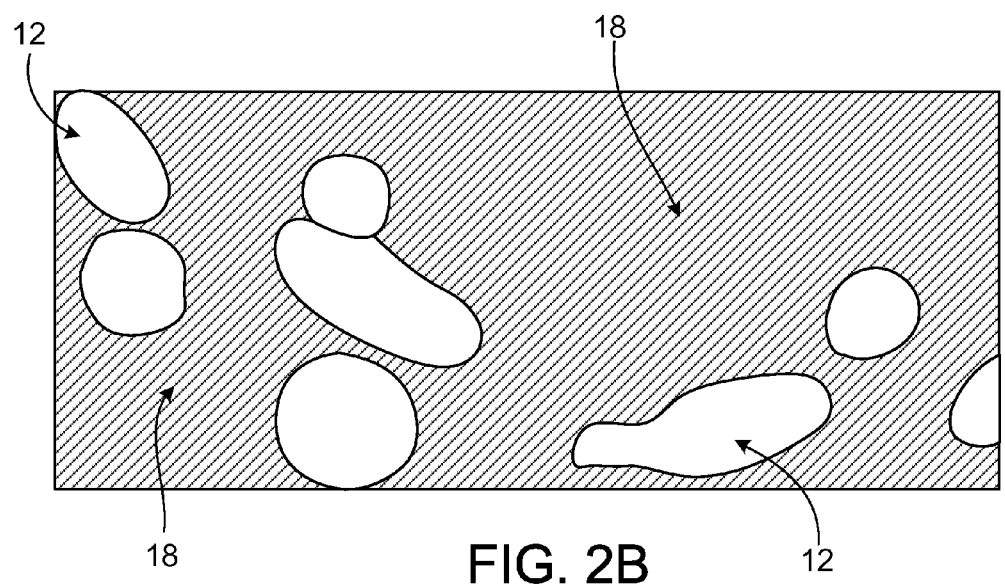
Figure 6A:
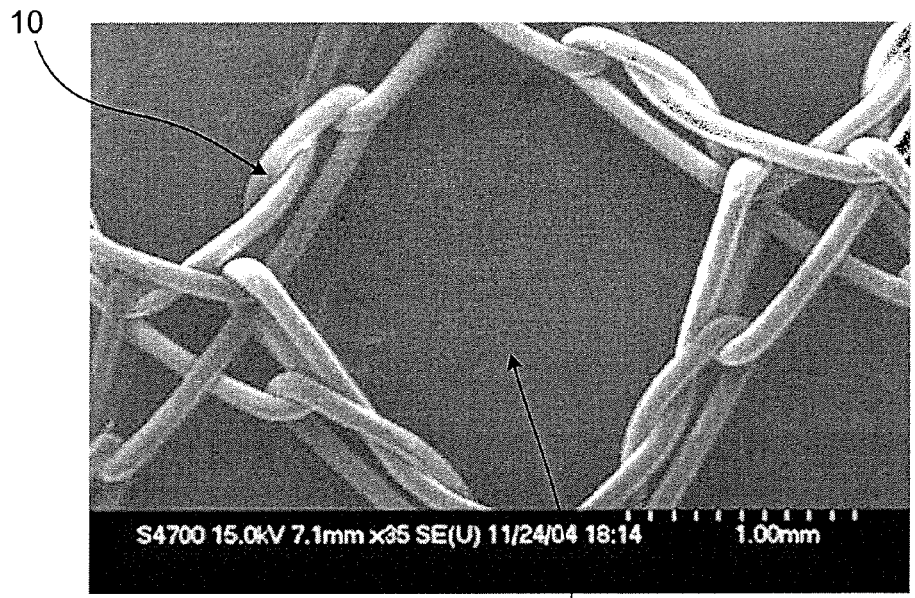
FIGS. 6A-6C are scanning electron micrographs of a polypropylene mesh made as described in Example 3, with no condensation, at 35×, 80×, and 70×, respectively.
Figure 6B:
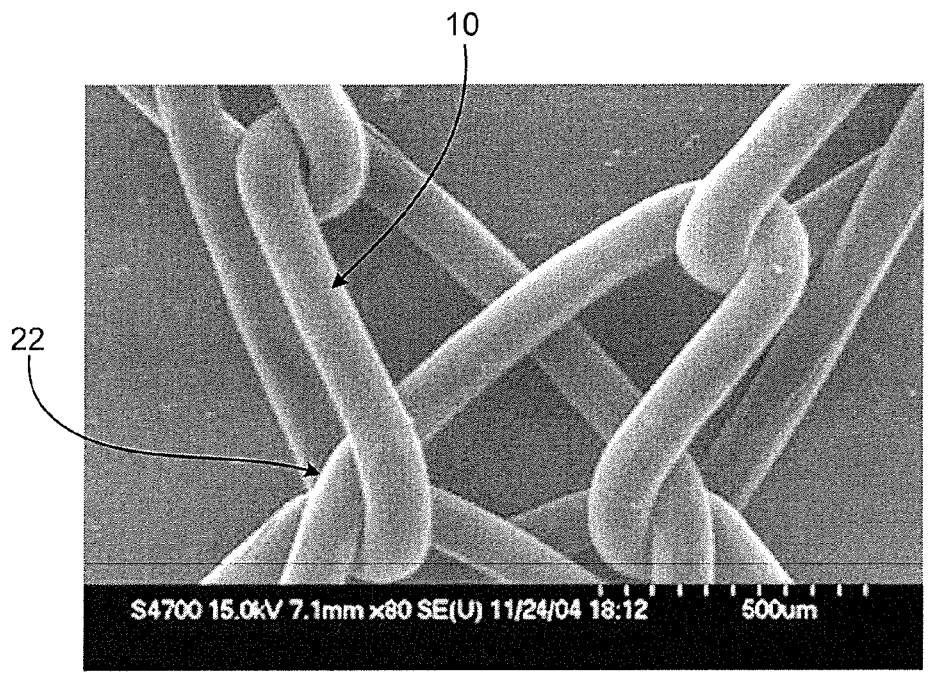
Figure 6C:
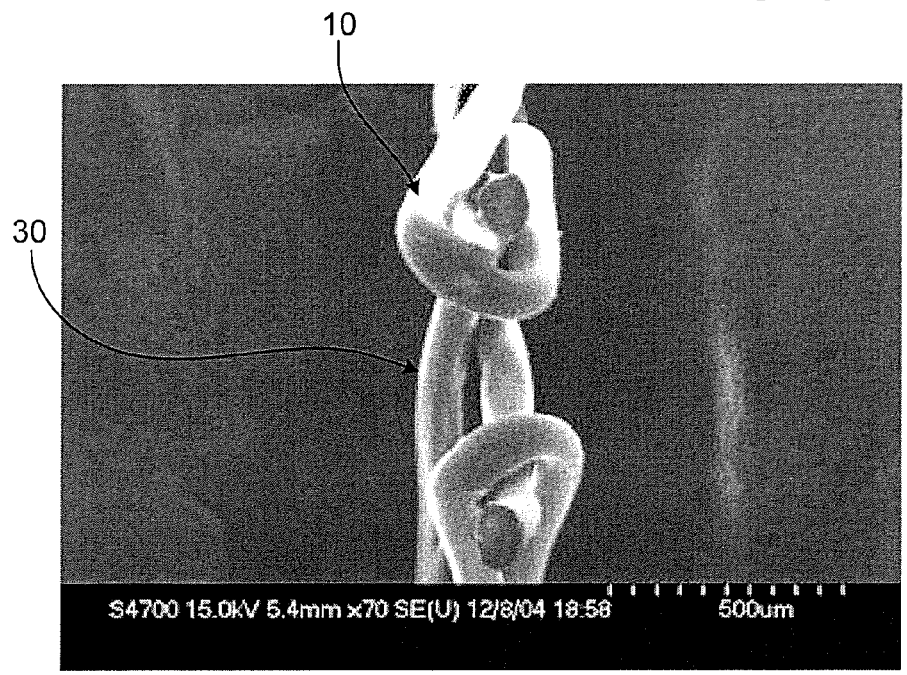
Figure 6D:
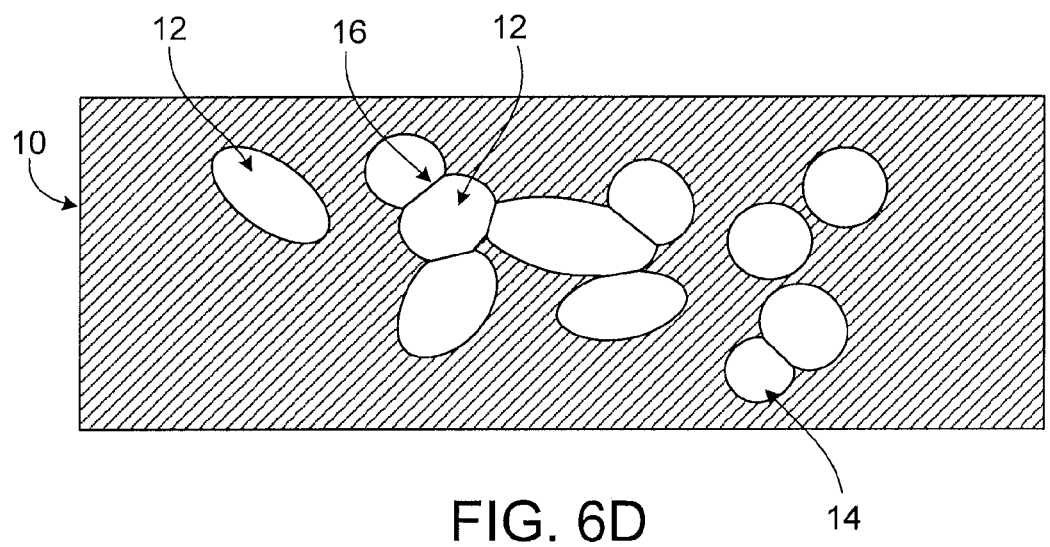
FIG. 6D is a light micrograph of a polypropylene mesh made as described in Example 3, with no condensation, cross section shown at 125×.

Referring to FIGS. 2A and 2B, schematics of an uncondensed surgical mesh in cross section corresponding to the surgical mesh described in Example 3 and shown in FIG. 6D, monofilament fibres 10 have substantially round or oval perimeters and varying cross sectional area 12 depending upon the plane of the section. Upon implantation, monofilament fibres 10 are in contact with surrounding tissue 14. Where monofilament fibres 10 are in direct contact, a portion of the perimeter 16 is unavailable to contact surrounding tissue 14.

Figure 3A:
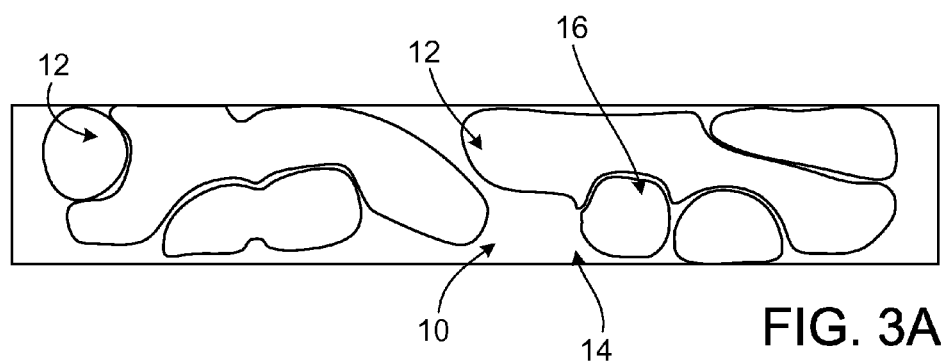
FIGS. 3A and 3B are cross sectional diagrams of the surgical mesh implant of FIGS. 2A and 2B following condensation.
Figure 3B:
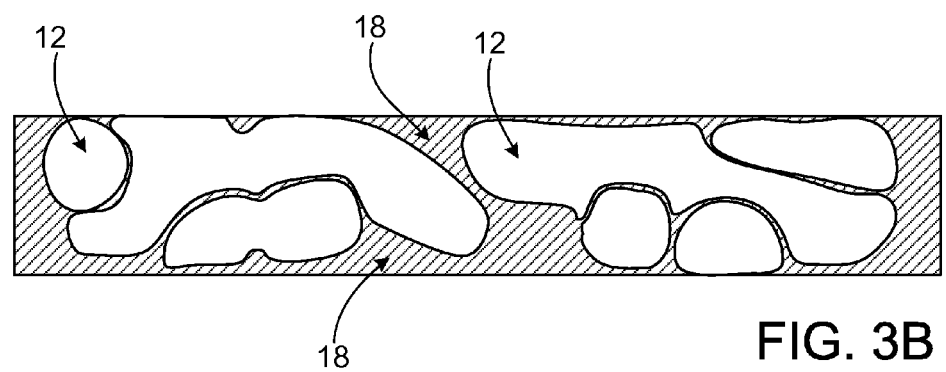
Figure 10A:
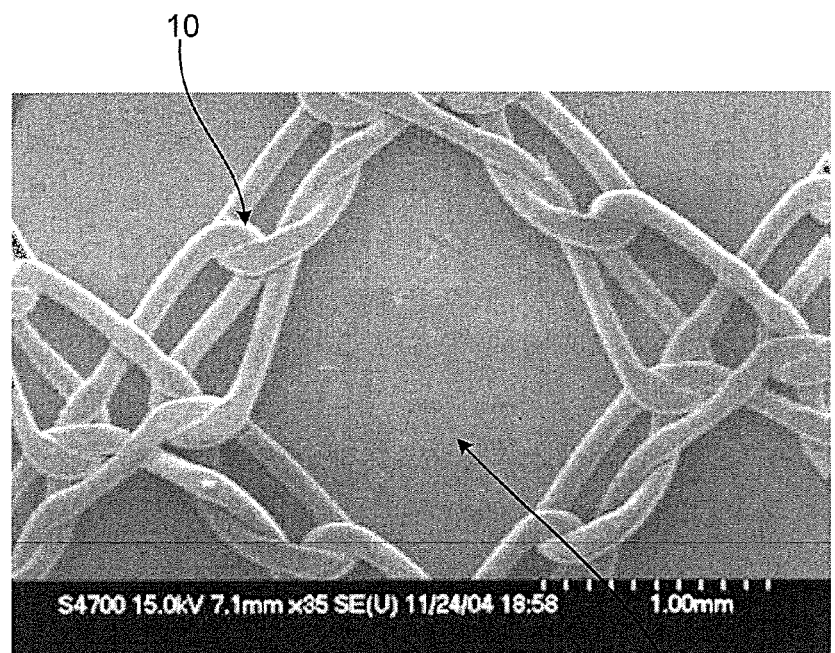
FIGS. 10A-10C are scanning electron micrographs of a polypropylene mesh made as described in Example 7, with condensation at a force of 75 N/cm$^2$, heat application, and vacuum, at 35×, 80×, and 70×, respectively.
Figure 10B:
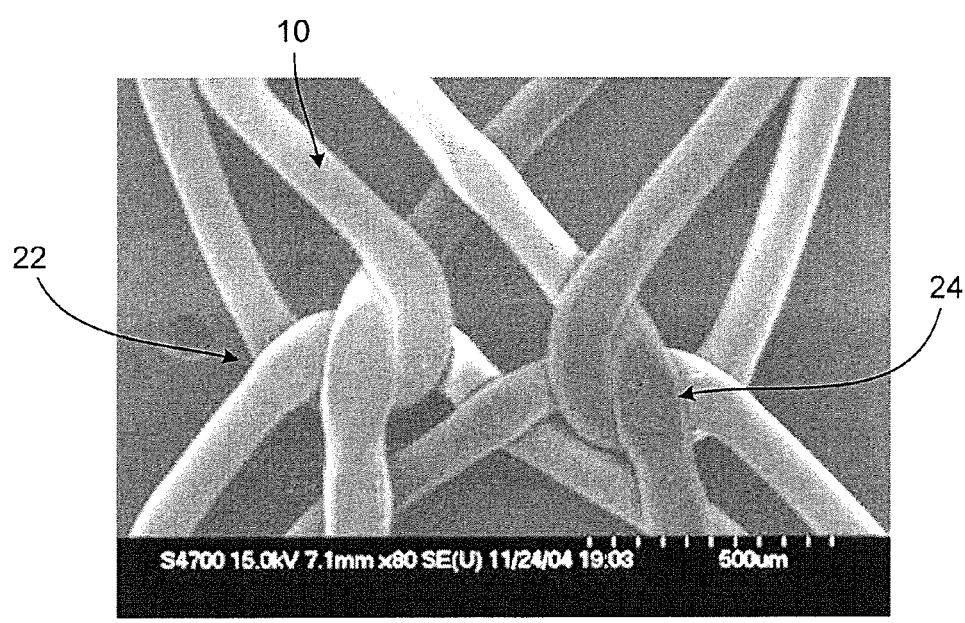
Figure 10C:
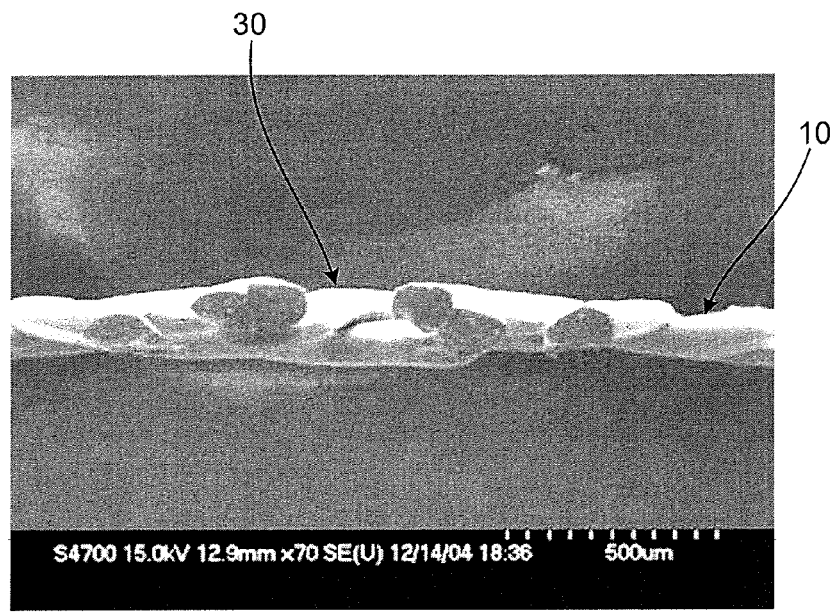
Figure 10D:
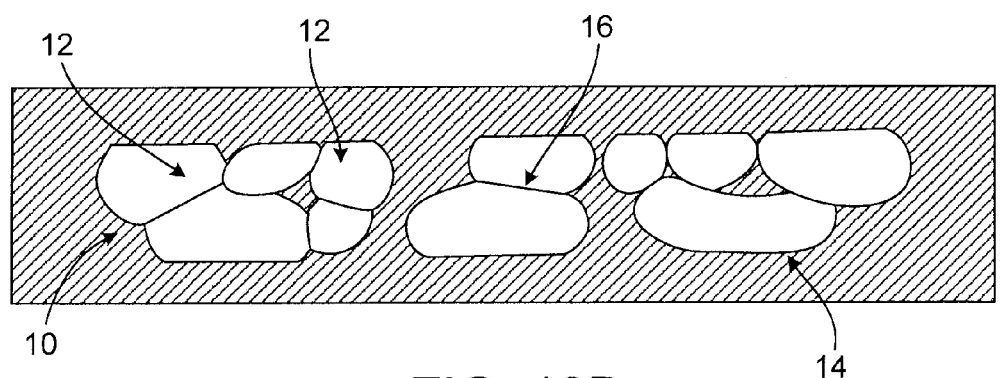
FIG. 10D is a light micrograph of a polypropylene mesh made as described in Example 7, with condensation at a force of 75 N/cm$^2$, heat application, and vacuum, cross section shown at 125×.

Referring to FIGS. 3A and 3B, schematics of a condensed surgical mesh in cross section corresponding to the surgical mesh described in Example 6 and shown in FIG. 10D, the perimeters of monofilament fibres 10 have been altered relative to those of the uncondensed mesh while the total cross sectional area remains constant. Thus, the value of the perimeter in contact with tissue upon implantation and the void area 18 within the implant available for tissue infiltration are both reduced in a condensed mesh relative to an uncondensed mesh.

Figure 4A:
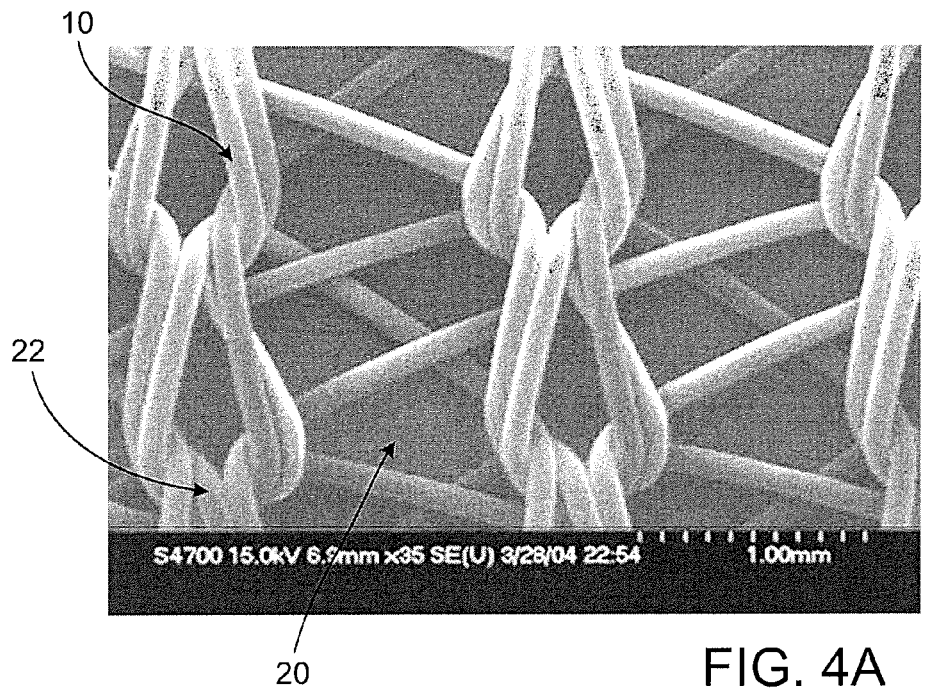
FIGS. 4A-4C are scanning electron micrographs of a surgical mesh before (FIG. 4A) and after (FIG. 4B) condensation and with an attached non-elastic element (FIG. 4C). The implant shown in FIG. 4C may be referred to as a composite implant sling.
Figure 4B:
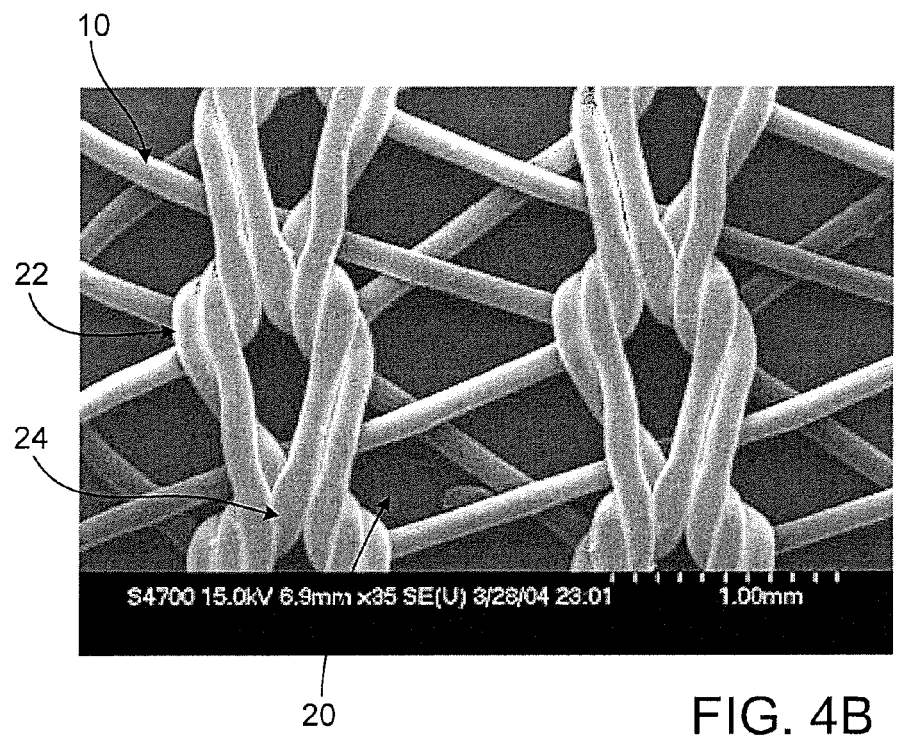
Figure 4C:
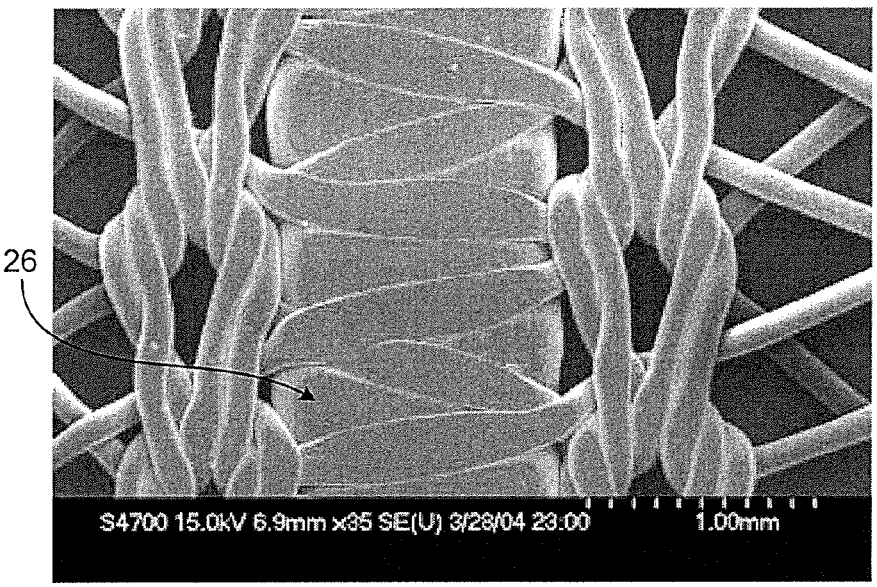

Referring to FIG. 4A, a scanning electron micrograph of uncondensed polypropylene surgical mesh, monofilament fibres 10 are used to knit a mesh of large pore 20 construction that permits tissue ingrowth upon implantation. Stitch loop intersections 22 are created during the knitting process. The surgical mesh is sold as Prolene™ Mesh (Ethicon, Somerville, N.J., USA). Referring to FIG. 4B, condensation zones 24 are created at stitch loop intersections 22 following the application of vacuum, heat, and pressure, which compresses monofilament fibres 10 into shapes having lower profiles. Nonelastic fibres 26 are applied to the surgical mesh of FIG. 4C to generate a composite implant.

Figure 5A:
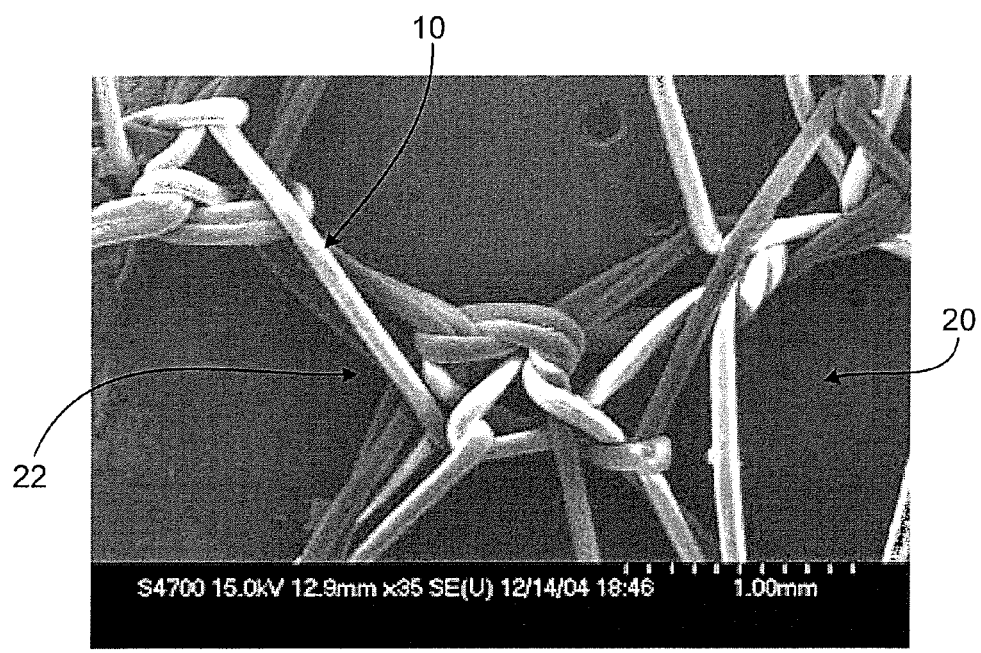
FIGS. 5A and 5B are scanning electron micrographs of Prolene™ Soft Mesh (no condensation) 35× and Mersilene™ Mesh (no condensation) 35×, respectively.
Figure 5B:
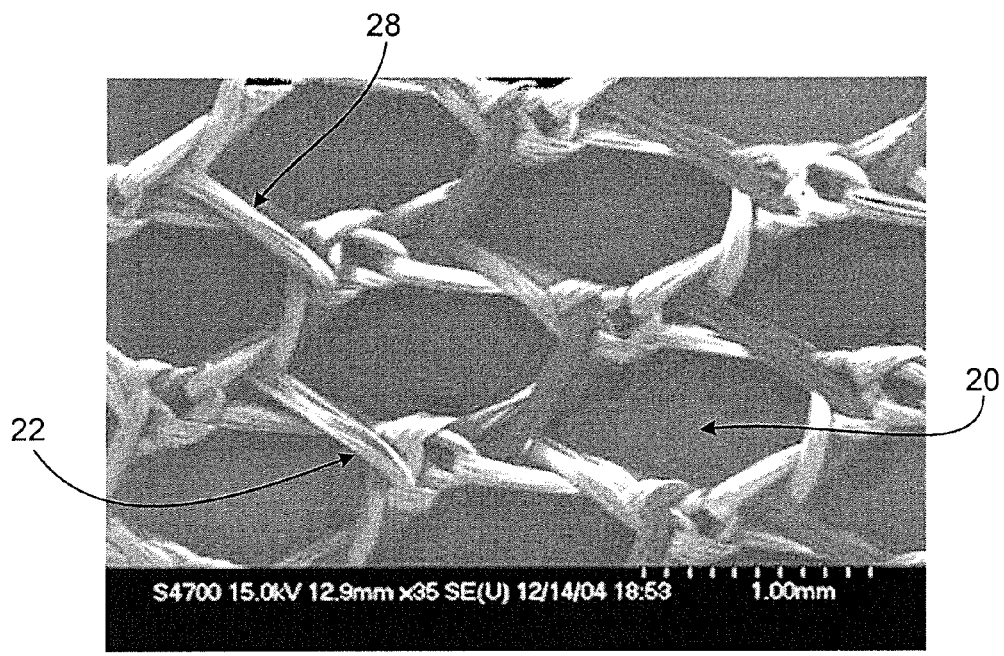

Referring to FIG. 5A, a scanning electron micrograph of uncondensed polypropylene surgical mesh, monofilament fibres 10 are used to knit a mesh of large pore 20 construction that permits tissue ingrowth upon implantation. Stitch loop intersections 22 are created during the knitting process. The surgical mesh is sold as Prolene Soft™ Mesh (Ethicon, Somerville, N.J., USA). Referring to FIG. 5B, a scanning electron micrograph of uncondensed polypropylene surgical mesh, multifilament fibres 28 are used to knit a mesh of large pore 20 construction that permits tissue ingrowth upon implantation. Stitch loop intersections 22 are created during the knitting process. The surgical mesh is sold as Mersilene™ Mesh (Ethicon, Somerville, N.J., USA).

Referring to FIGS. 6A and 6B, scanning electron micrographs of uncondensed polypropylene mesh are shown at 35× and 80×, respectively. Monofilament fibres 10 are used to knit the mesh into a large pore 20 construction which permits tissue ingrowth upon implantation. Stitch loop intersections 22 are created during the knitting process. Referring to FIG. 6C, a scanning electron micrograph of uncondensed polypropylene mesh, the surgical mesh thickness profile 30 is determined by the distance between monofilament fibres 10 from a first side to a second side of the surgical mesh (e.g., from the back to the front). Referring to FIG. 6D, a light micrograph of an uncondensed surgical mesh cross section shown at 10×. The area of void for tissue infiltration is identified and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 7A:
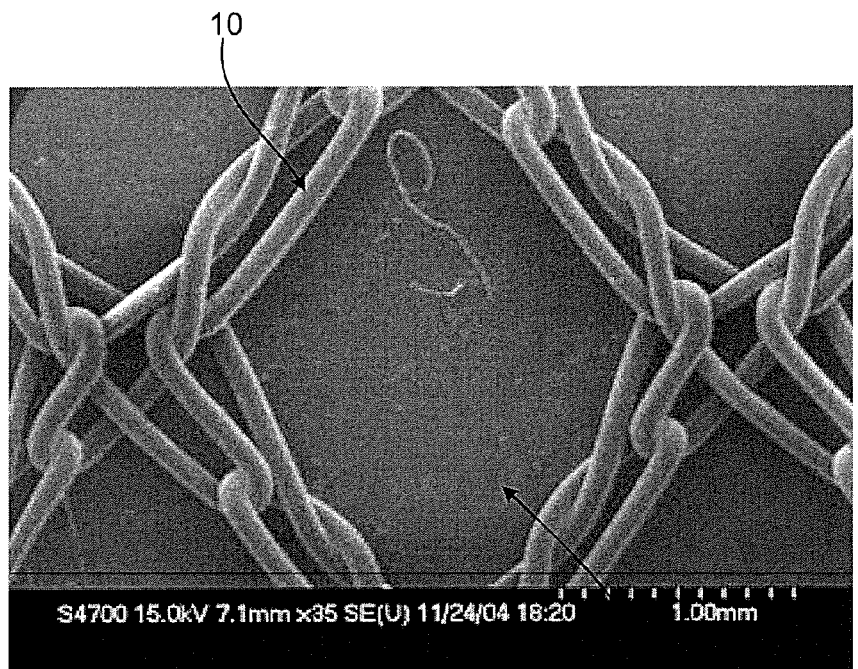
FIGS. 7A-7C are scanning electron micrographs of a polypropylene mesh made as described in Example 4, with condensation at a force of 10 N/cm$^2$, heat application, and vacuum, at 35×, 80×, and 70×, respectively.
Figure 7B:
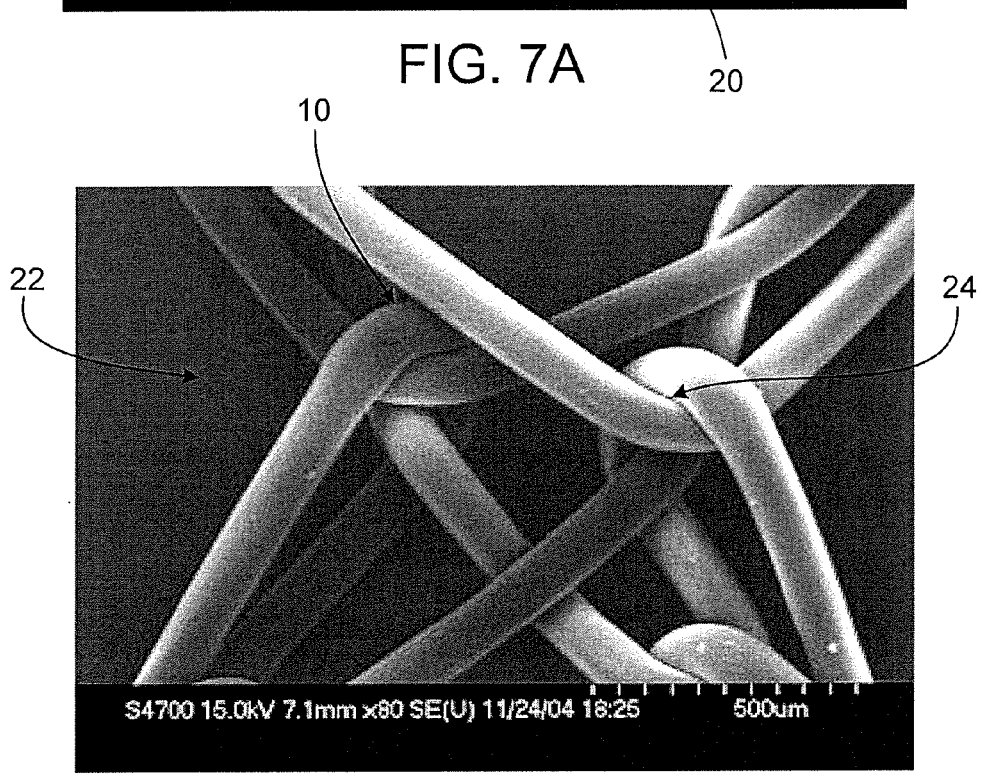
Figure 7C:
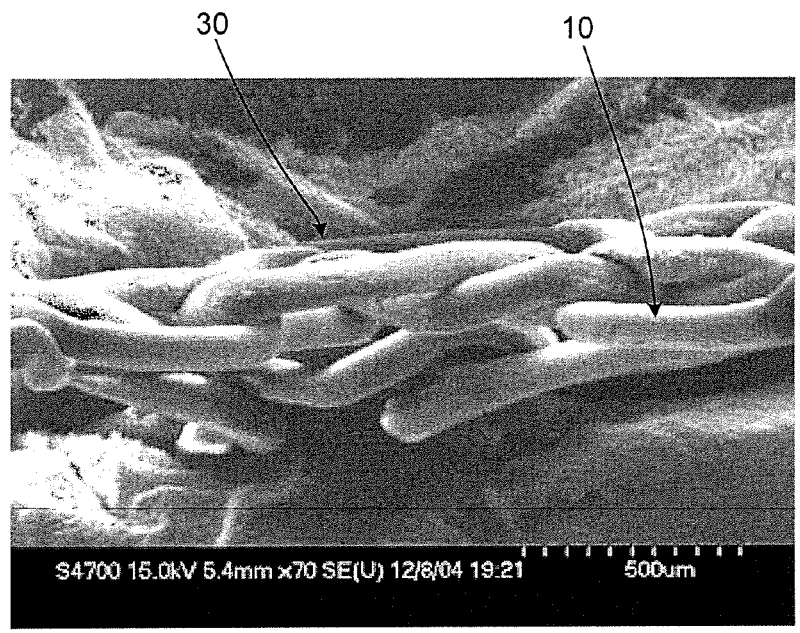
Figure 7D:
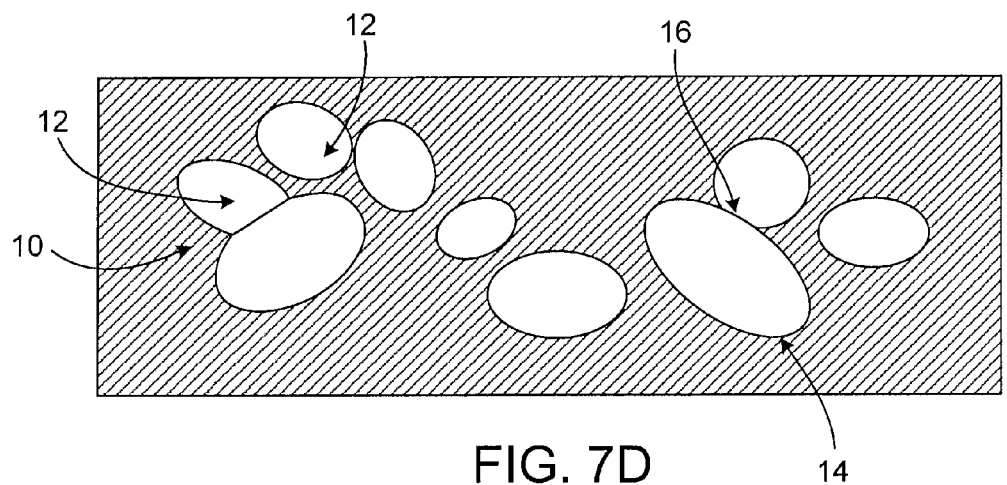
FIG. 7D is a light micrograph of a polypropylene mesh made as described in Example 4, with condensation at a force of 10 N/cm$^2$, heat application, and vacuum, cross section shown at 125×.

Referring to FIGS. 7A and 7B, scanning electron micrographs of polypropylene mesh condensed under vacuum, heat, and a force of 10 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are beginning to appear. Referring to FIG. 7C, a scanning electron micrograph of a cross section of a polypropylene mesh condensed under vacuum, heat, and a force of 10 N/cm$^2$, magnified 70×. The surgical mesh thickness profile 30 is determined by the distance between monofilament fibres 10 at the front and back of the condensed surgical mesh. Referring to FIG. 7D, a light micrograph of a surgical mesh cross section condensed under vacuum, heat, and a force of 10 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 8A:
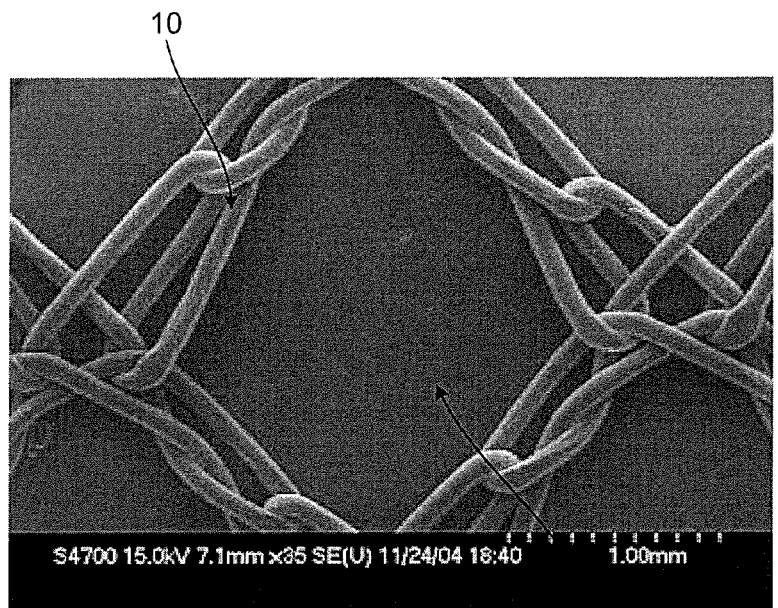
FIGS. 8A-8C are scanning electron micrographs of a polypropylene mesh made as described in Example 5, with condensation at a force of 25 N/cm$^2$, heat application, and vacuum, at 35×, 80×, and 70×, respectively.
Figure 8B:
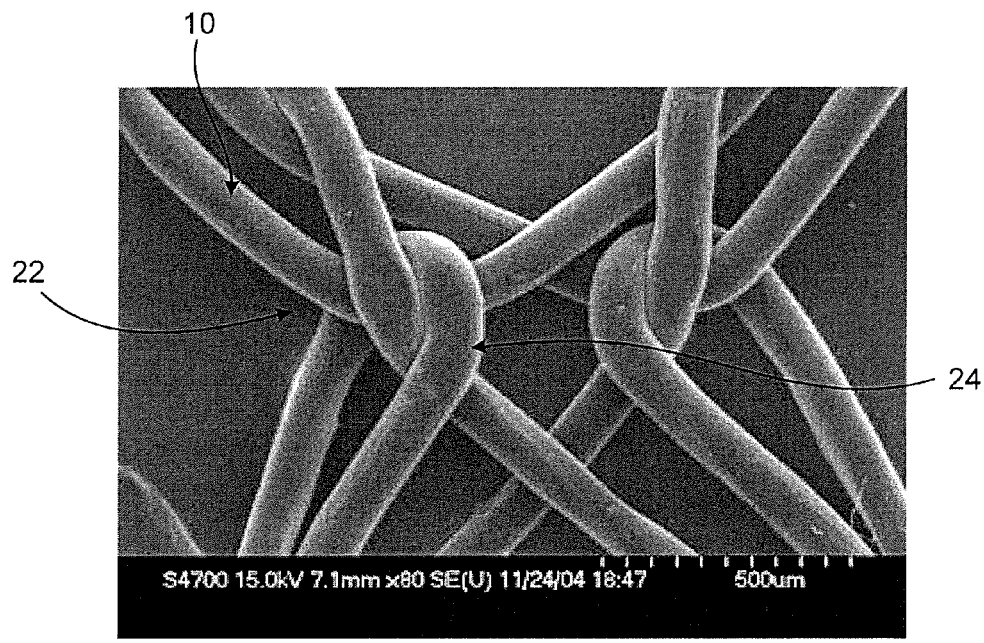
Figure 8C:
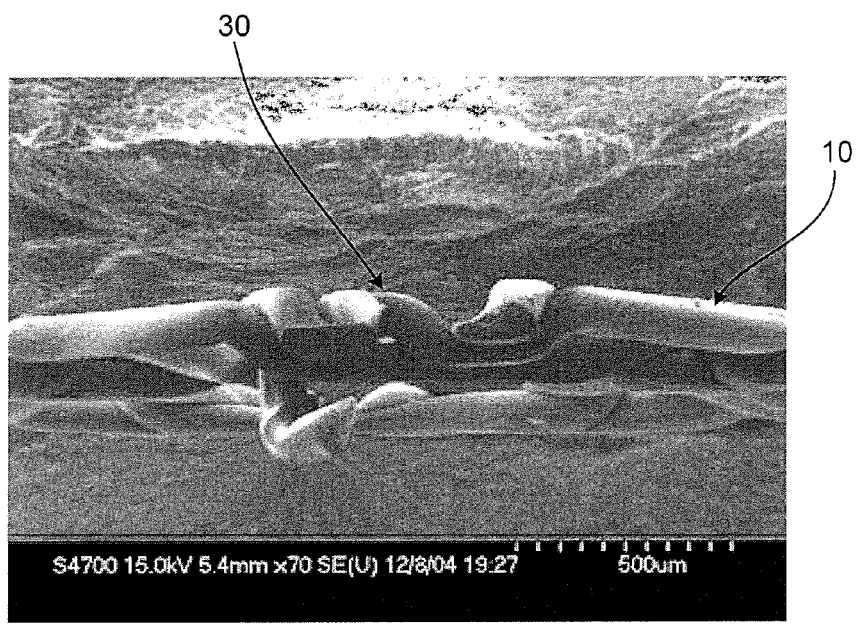
Figure 8D:
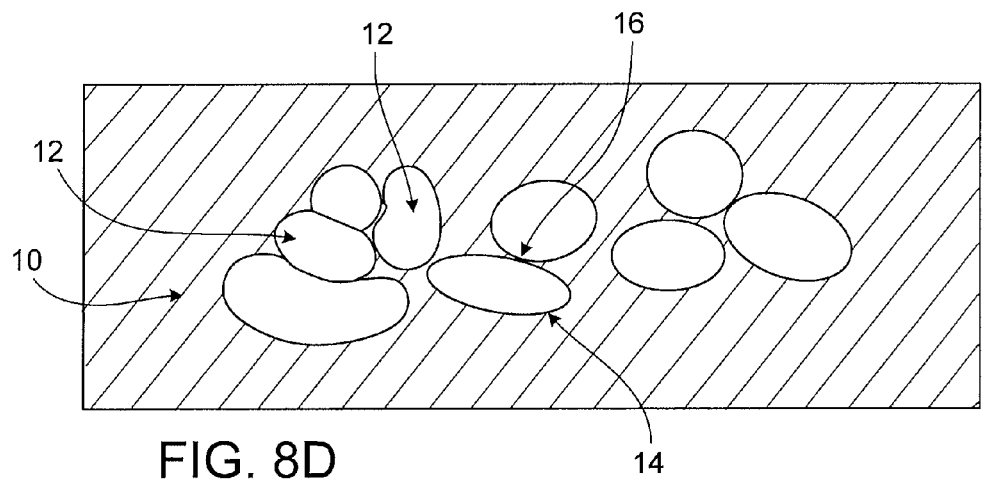
FIG. 8D is a light micrograph of a polypropylene mesh made as described in Example 5, with condensation at a force of 25 N/cm$^2$, heat application, and vacuum, cross section shown at 125×.

Referring to FIGS. 8A and 8B, scanning electron micrographs of polypropylene mesh condensed under vacuum, heat, and a force of 25 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are shown. Referring to FIG. 8C, a scanning electron micrograph of a cross section of a polypropylene mesh condensed under vacuum, heat, and a force of 25 N/cm$^2$, magnified 70×. The surgical mesh thickness profile 30 is determined by the distance between monofilament fibres 10 at the front and back of the condensed surgical mesh. Referring to FIG. 8D, a light micrograph of a surgical mesh cross section Condensed under vacuum, heat, and a force of 25 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 9A:
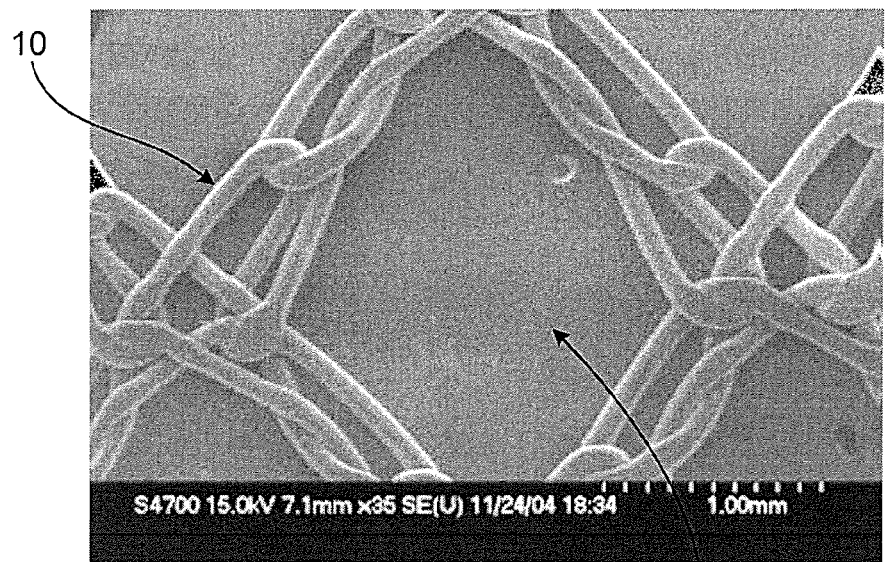
FIGS. 9A-9C are scanning electron micrographs of a polypropylene mesh made as described in Example 6, with condensation at a force of 50 N/cm$^2$, heat application, and vacuum, at 35×, 80×, and 70×, respectively.
Figure 9B:
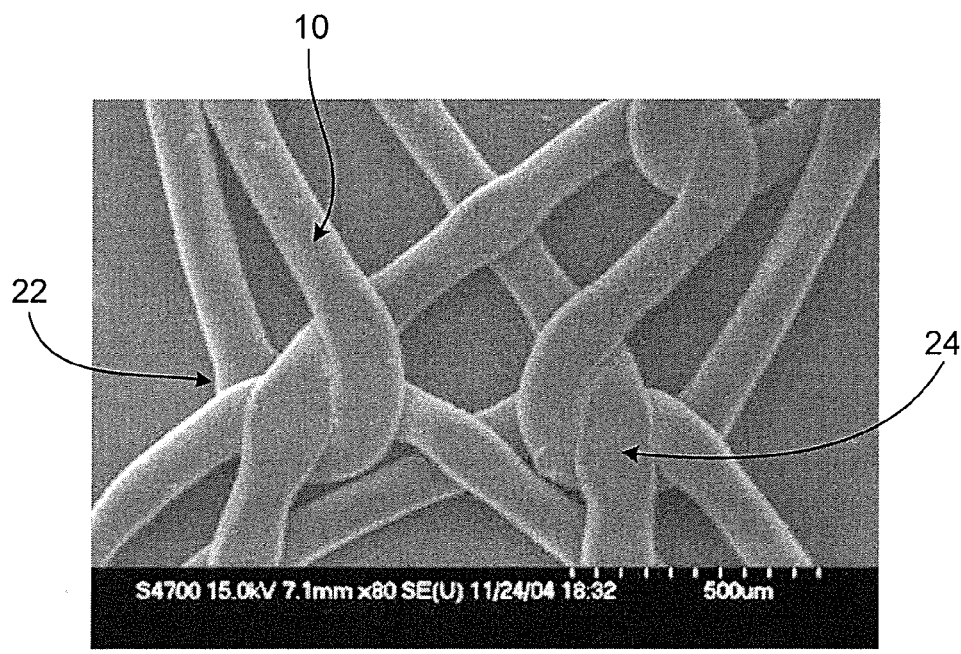
Figure 9C:
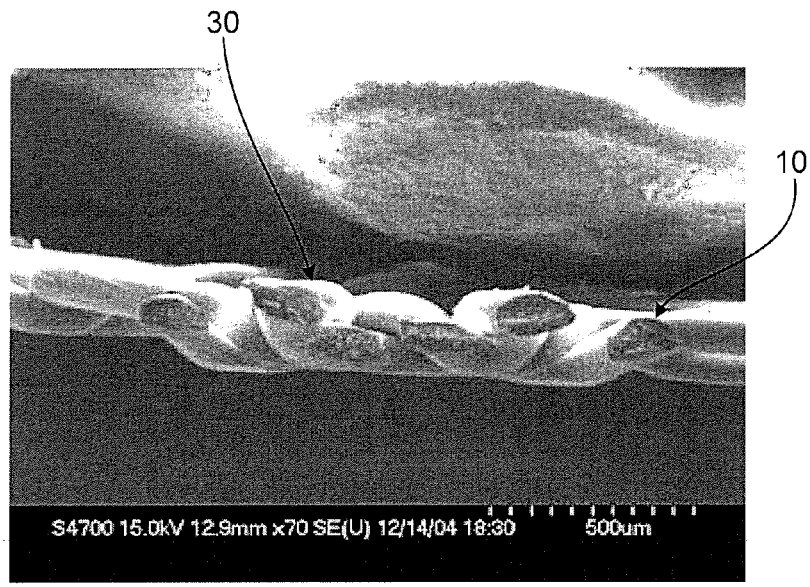
Figure 9D:
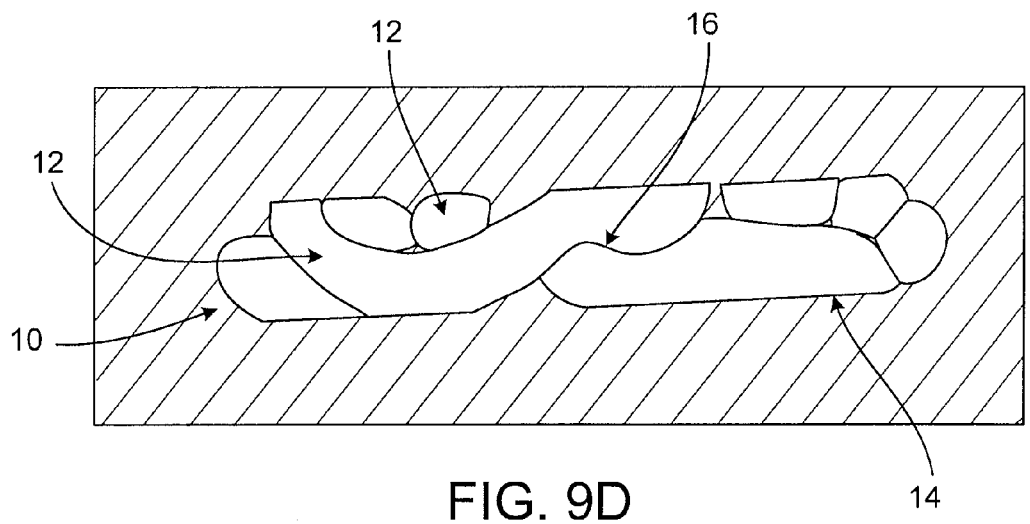
FIG. 9D is a light micrograph of a polypropylene mesh made as described in Example 6, with condensation at a force of 50 N/cm$^2$, heat application, and vacuum, cross section shown at 125×.

Referring to FIGS. 9A and 9B, scanning electron micrographs of polypropylene mesh condensed under vacuum, heat, and a force of 50 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are readily apparent. Referring to FIG. 9C, a scanning electron micrograph of a cross section of a polypropylene mesh condensed under vacuum, heat, and a force of 50 N/cm$^2$, magnified 70×. The surgical mesh thickness profile 30 is determined by the distance between monofilament fibres 10 at the front and back of the condensed surgical mesh. Referring to FIG. 9D, a light micrograph of a surgical mesh cross section condensed under vacuum, heat, and a force of 50 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Referring to FIGS. 10A and 10B, scanning electron micrographs of polypropylene mesh condensed under vacuum, heat, and a force of 75 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are readily visible. Referring to FIG. 10C, a scanning electron micrograph of a cross section of a polypropylene mesh condensed under vacuum, heat, and a force of 75 N/cm$^2$, magnified 70×. The surgical mesh thickness profile 30 is determined by the distance between monofilament fibres 10 at the front and back of the condensed surgical mesh. Referring to FIG. 10D, a light micrograph of a surgical mesh cross section condensed under vacuum, heat, and a force of 75 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 11A:
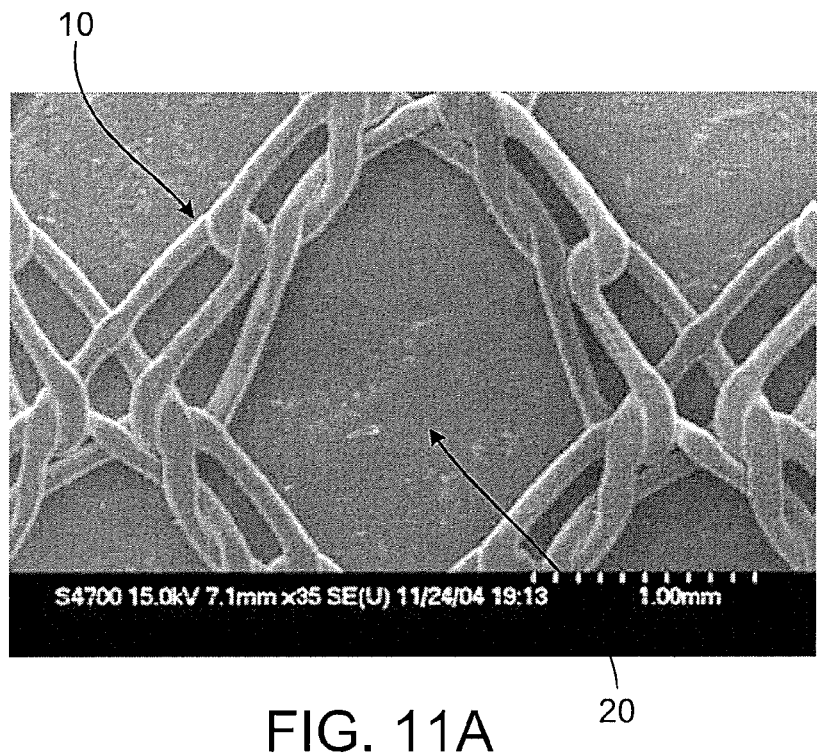
FIGS. 11A-11C are scanning electron micrographs of a polypropylene mesh made as described in Example 8, with condensation at a force of 100 N/cm$^2$, heat application, and vacuum, at 35×, 80×, and 70×, respectively.
Figure 11B:
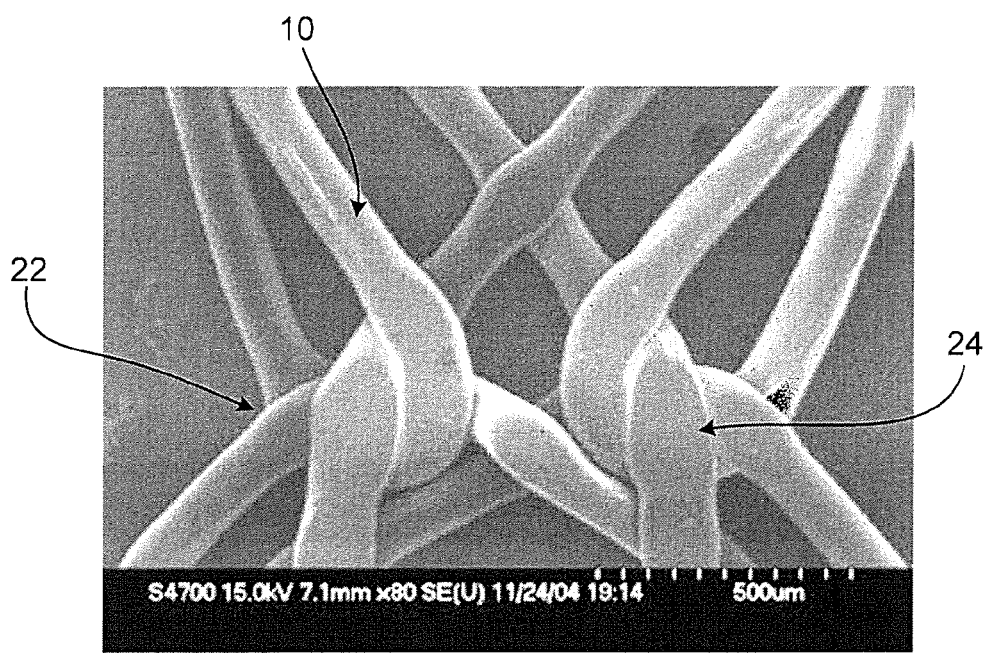
Figure 11C:
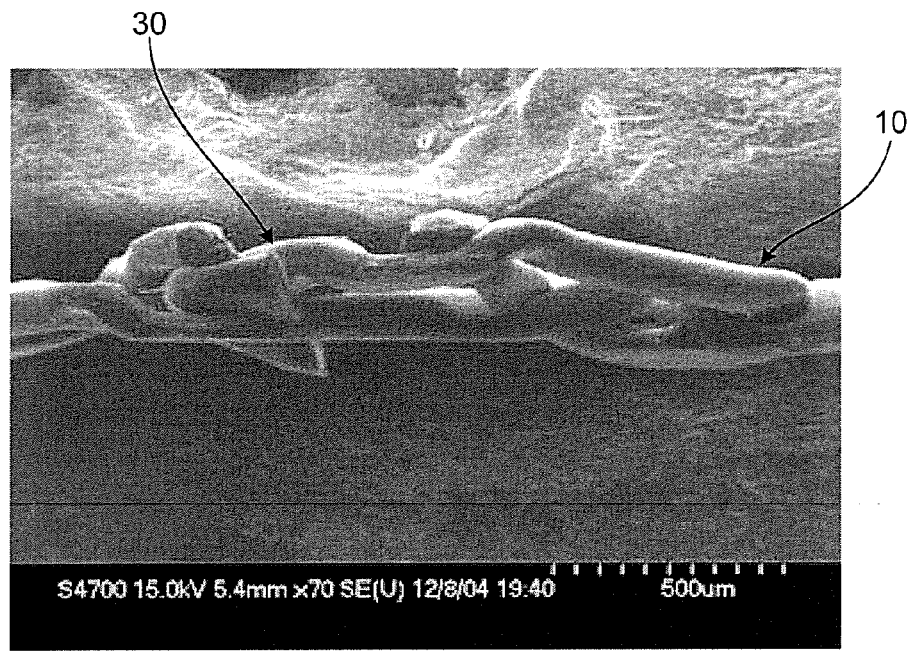
Figure 11D:
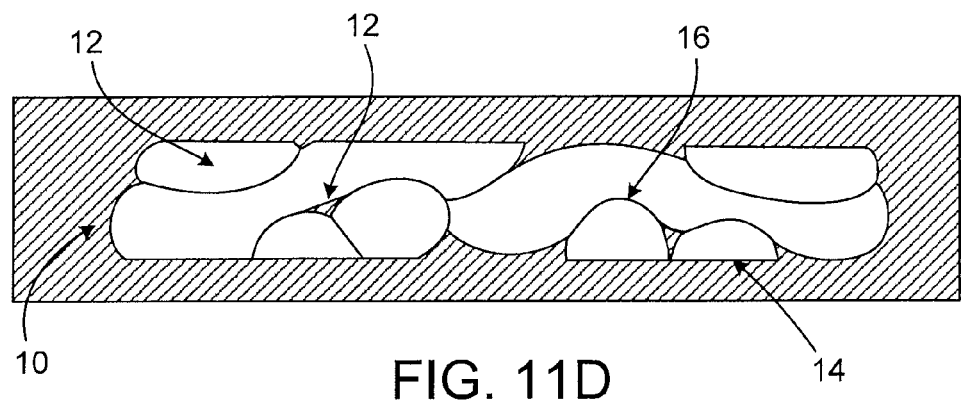
FIG. 11D is a light micrograph of a polypropylene mesh made as described in Example 4, with condensation at a force of 100 N/cm$^2$, heat application, and vacuum, cross section shown at 125×.

Referring to FIGS. 11A and 11B, scanning electron micrographs of polypropylene mesh condensed under vacuum, heat, and a force of 100 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are readily visible. Referring to FIG. 11C, a scanning electron micrograph of a cross section of a polypropylene mesh condensed under vacuum, heat, and a force of 100 N/cm$^2$, magnified 70×. The surgical mesh thickness profile 30 is determined by the distance between monofilament fibres 10 at the front and back of the condensed surgical mesh. Referring to FIG. 11D, a light micrograph of a surgical mesh cross section condensed under vacuum, heat, and a force of 100 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 12A:
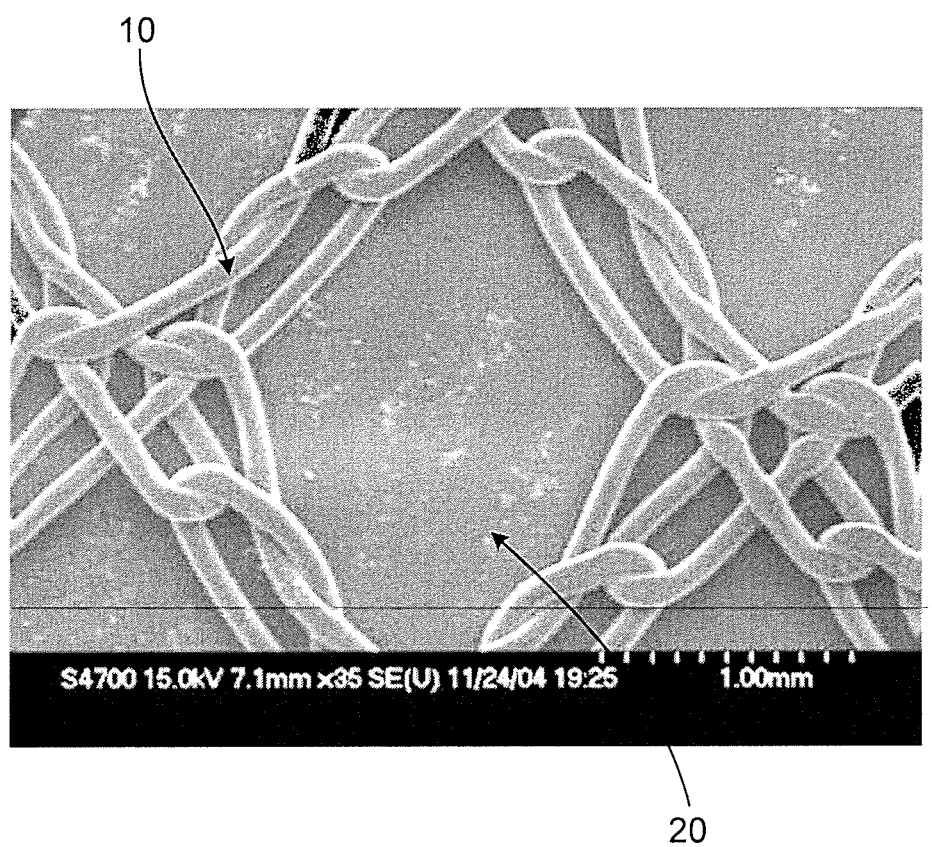
FIGS. 12A-12C are scanning electron micrographs of a polypropylene mesh made as described in Example 9, with condensation at a force of 125 N/cm$^2$, heat application, and vacuum, at 35×, 80×, and 70×, respectively.
Figure 12B:
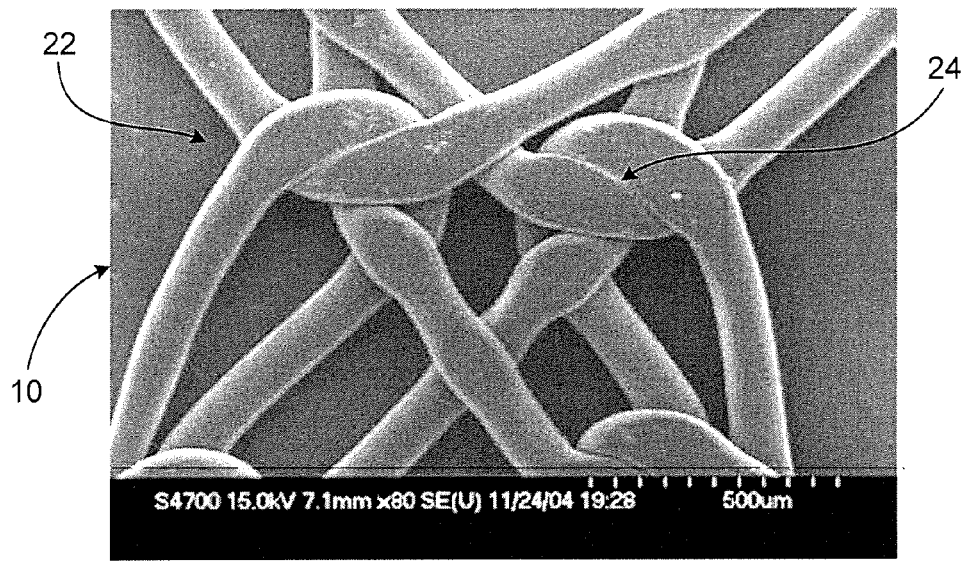
Figure 12C:
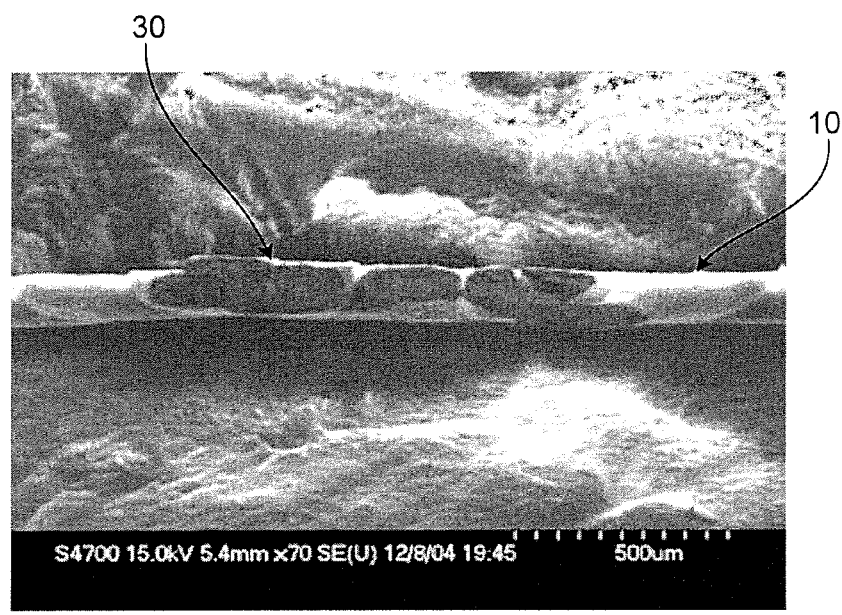
Figure 12D:
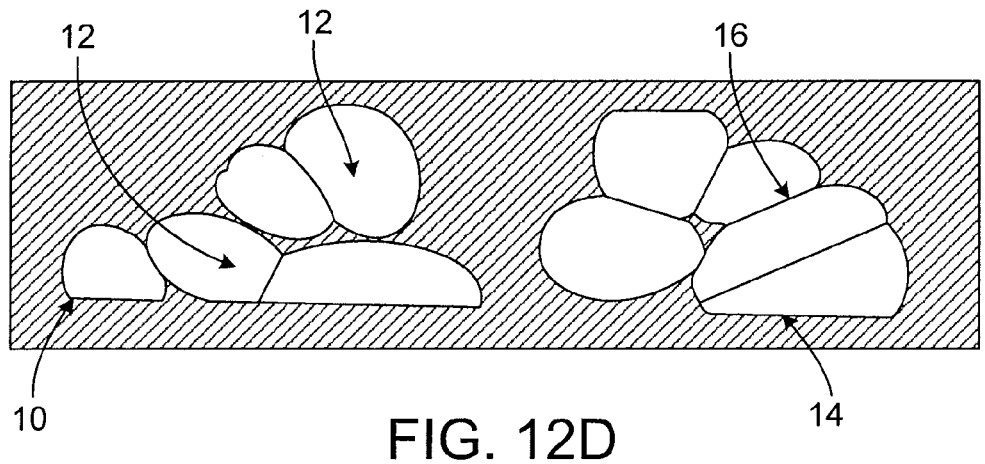
FIG. 12D is a light micrograph of a polypropylene mesh made as described in Example 9, with condensation at a force of 125 N/cm$^2$, heat application, and vacuum, cross section shown at 125×.

Referring to FIGS. 12A and 12B, scanning electron micrographs of polypropylene mesh condensed under vacuum, heat, and a force of 125 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are readily visible. Referring to FIG. 12C, a scanning electron micrograph of a cross section of a polypropylene mesh condensed under vacuum, heat, and a force of 125 N/cm$^2$, magnified 70×. The surgical mesh thickness profile 30 is determined by the distance between monofilament fibres 10 at the front and back of the condensed surgical mesh. Referring to FIG. 12D, a light micrograph of a surgical mesh cross section condensed under vacuum, heat, and a force of 125 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 13A:
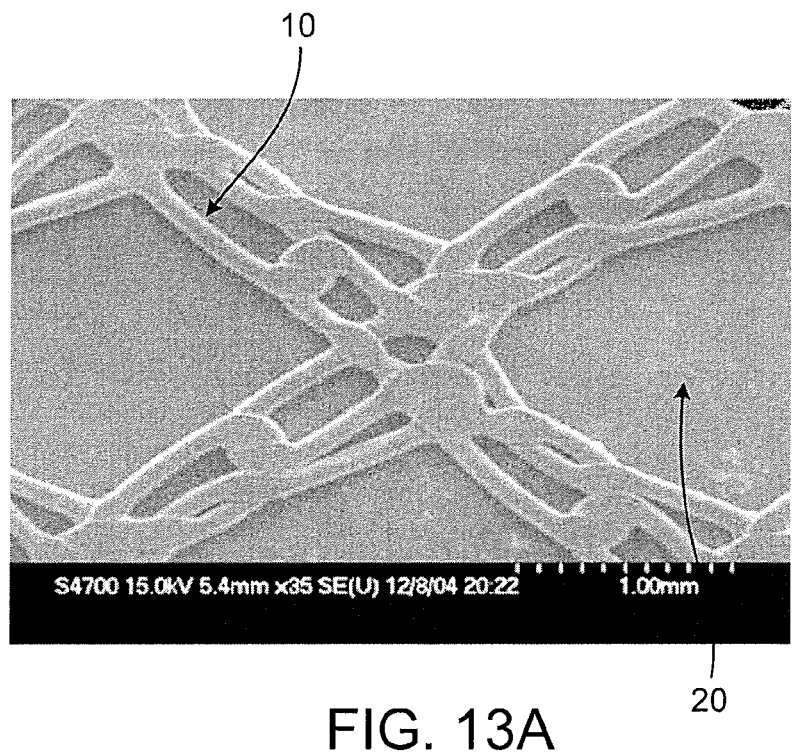
FIGS. 13A-13C are scanning electron micrographs of a polypropylene mesh made as described in Example 10, with condensation at a force of 250 N/cm$^2$, heat application, and vacuum, at 35×, 80×, and 70×, respectively.
Figure 13B:
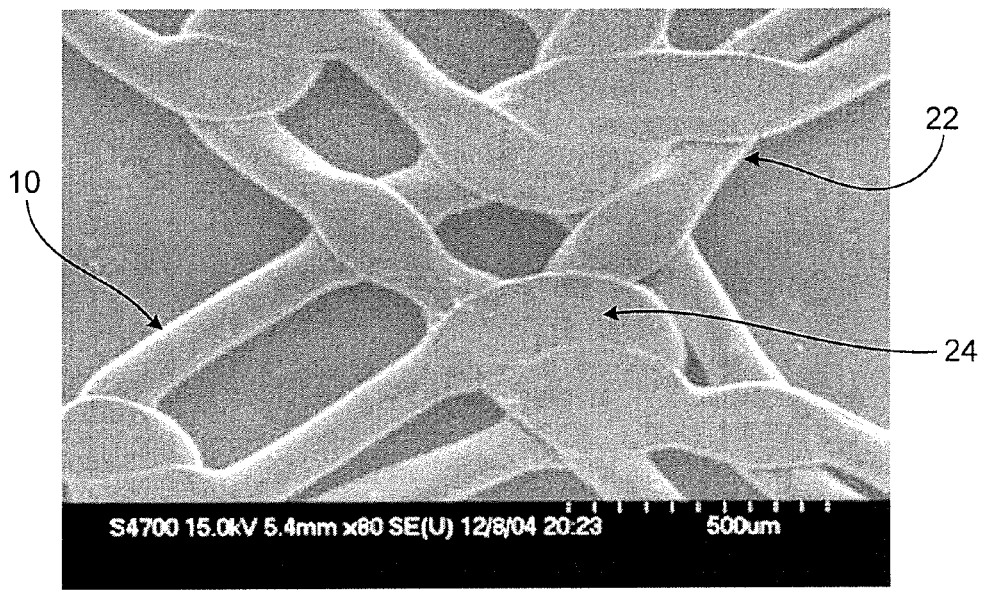
Figure 13C:
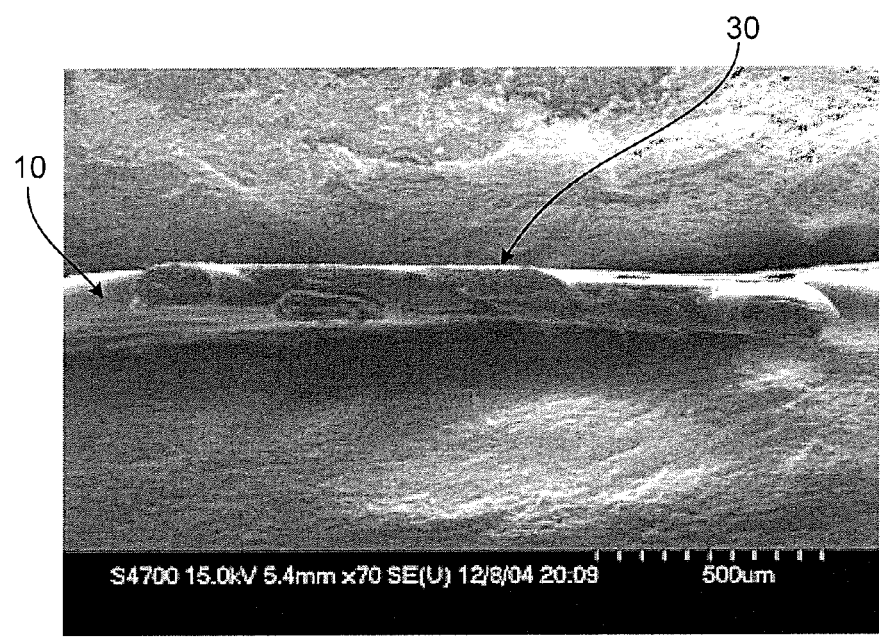
Figure 13D:
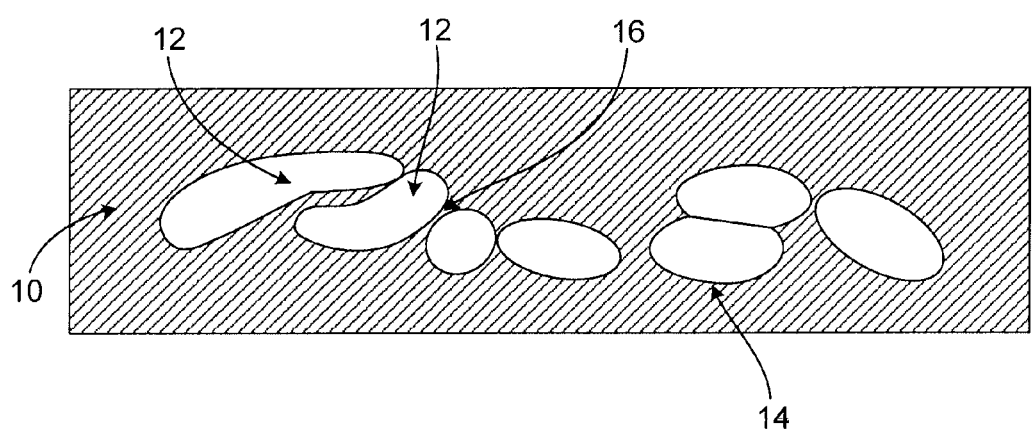
FIG. 13D is a light micrograph of a polypropylene mesh made as described in Example 10, with condensation at a force of 250 N/cm$^2$, heat application, and vacuum, cross section shown at 125×.

Referring to FIGS. 13A and 13B, scanning electron micrographs of polypropylene mesh condensed under vacuum, heat, and a force of 250 N/cm$^2$, magnified 35× and 80×, respectively. Monofilament fibres 10 are used to knit the mesh into a large pore 20 construction which permits tissue ingrowth. Stitch loop intersections 22 are created during the knitting process. Condensation zones 24 are readily visible. Referring to FIG. 13C, a scanning electron micrograph of a cross section of a polypropylene mesh condensed under vacuum, heat, and a force of 250 N/cm$^2$, magnified 70×. The surgical mesh thickness profile 30 is determined by the distance between monofilament fibres 10 at the front and back of the condensed surgical mesh. Referring to FIG. 12D, a light micrograph of a surgical mesh cross section condensed under vacuum, heat, and a force of 250 N/cm$^2$ shown at 10×. The area of void for tissue infiltration is outlined and the monofilament fibres 10 having substantially round or oval perimeters and varying cross-sectional area 12 depending on the plane of the section. Where monofilament fibres 10 are in direct contact, a portion of the perimeter 16 is unavailable to contact surrounding tissue 14.

Figure 14A:
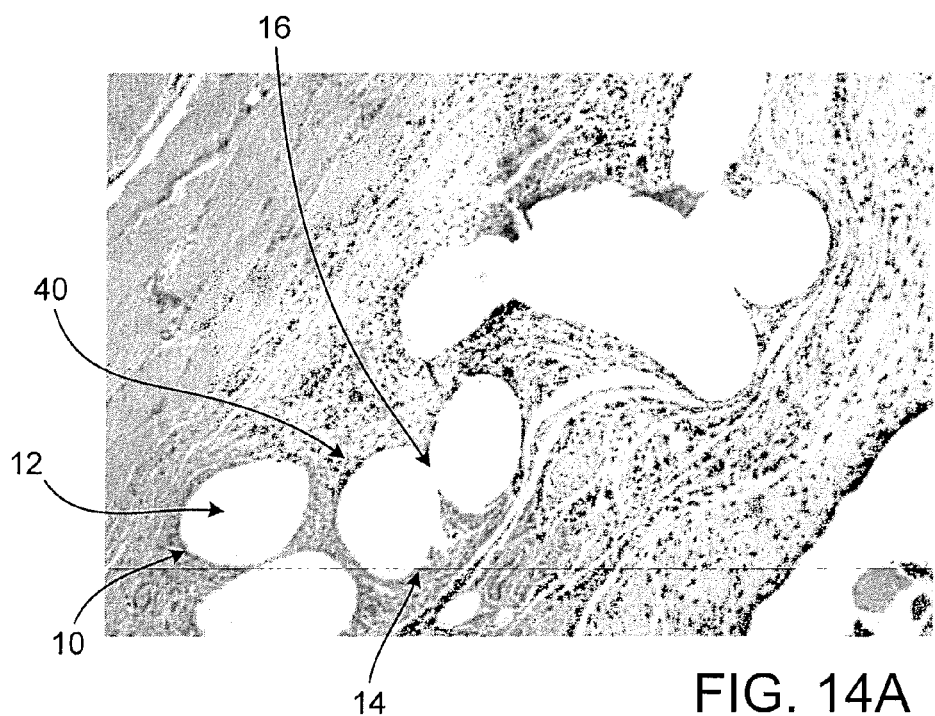
FIGS. 14A-14D are light micrographs of hematoxylin and eosin (H&E) stained 6 mil polypropylene meshes in cross section.
Figure 14B:
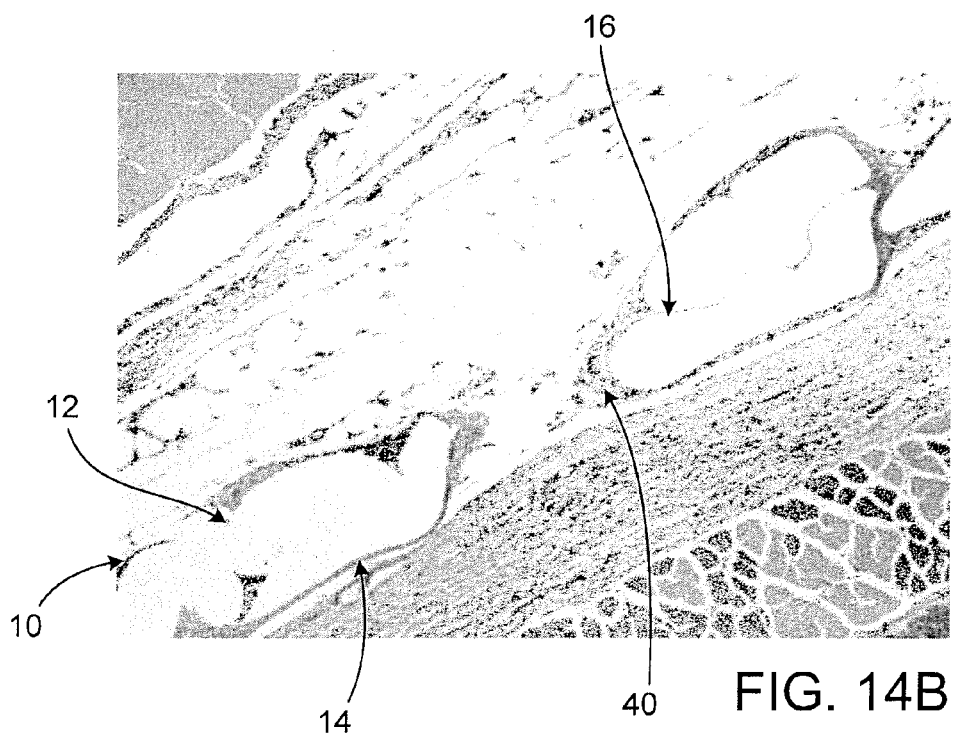
Figure 14C:
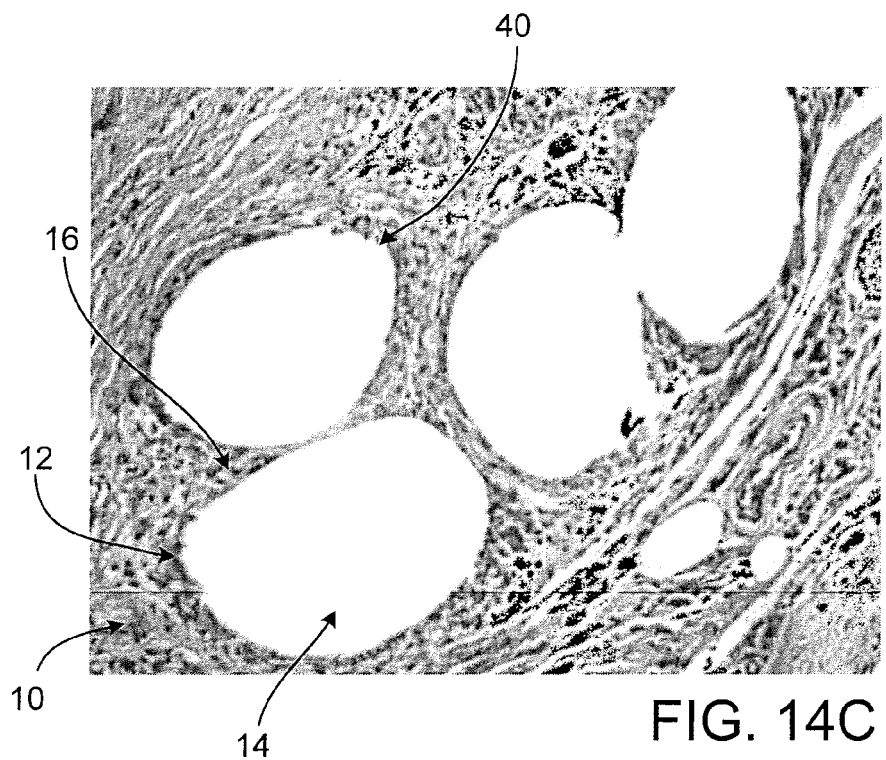
Figure 14D:
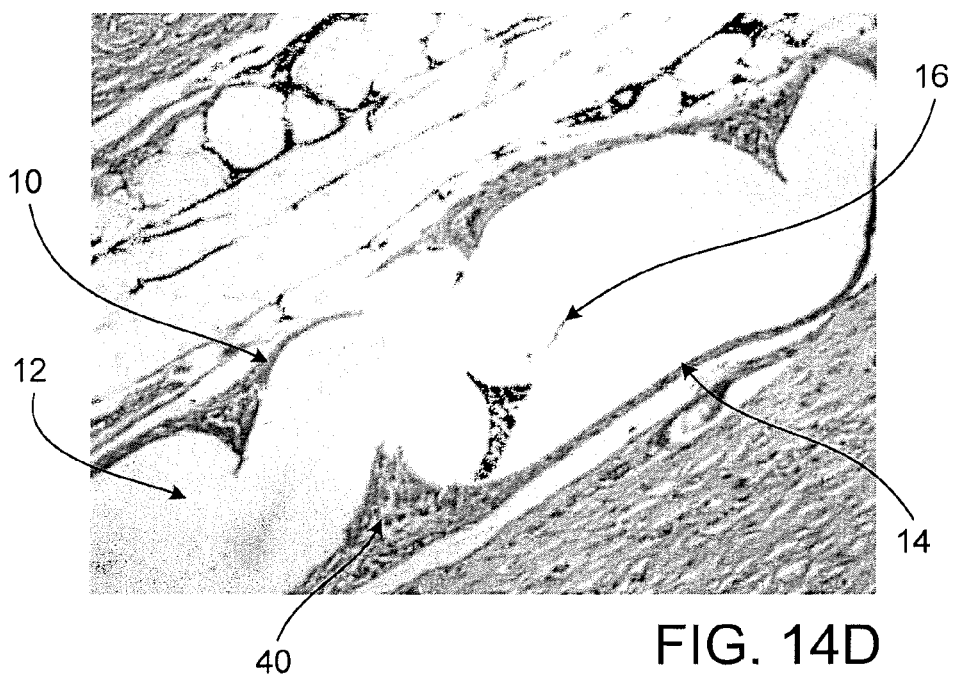

Referring to FIGS. 14A and 14C, a light micrograph of an H&E stained 6 mil uncondensed polypropylene mesh placed subcutaneously in tissue for 28 days, at magnifications of 100× and 200×, respectively. Monofilament fibres 10 and the cross sectional areas therein 12 are visible. Inflammatory cells 40 are present in surrounding tissue 14. Fewer inflammatory cells 40 are present around monofilament fibres 10 not in direct contact with tissue 16. Referring to FIGS. 14B and 14D, a light micrograph of an H&E stained 6 mil polypropylene mesh condensed under vacuum, heat, and a force of 75 N/cm$^2$ and placed subcutaneously in tissue for 28 days, at magnifications of 100× and 200×, respectively. Monofilament fibres 10 and the cross sectional areas therein 12 are visible. Inflammatory cells 40 are present in surrounding tissue 14. Fewer inflammatory cells 40 are present around monofilament fibres 10 not in direct contact with tissue 16.

Figure 15A:
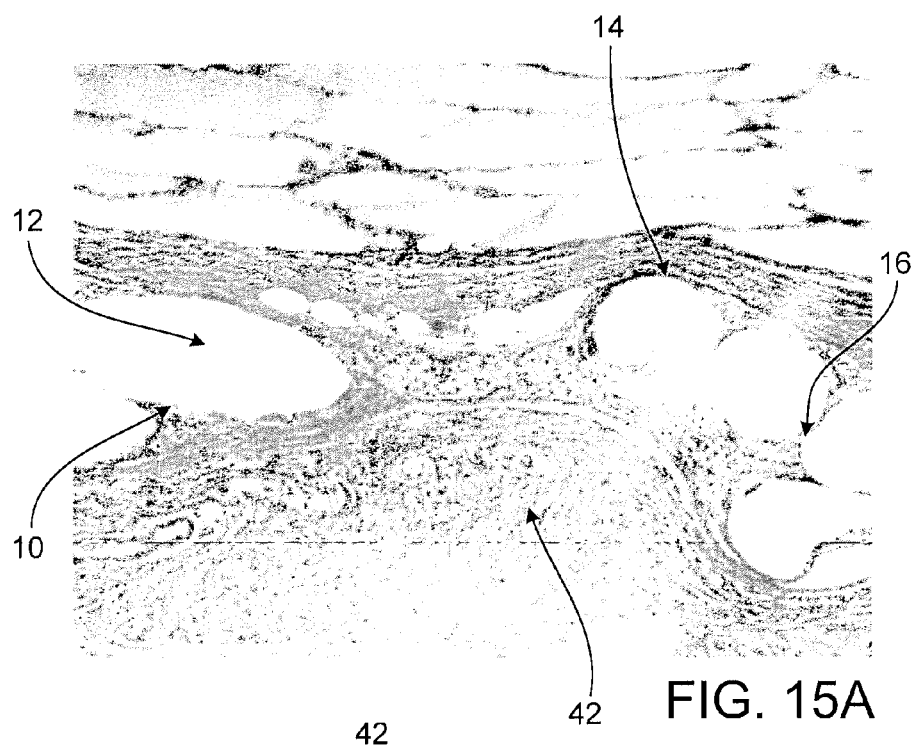
FIGS. 15A-15D are light micrographs of trichrome stained 6 mil polypropylene meshes in cross section.
Figure 15B:
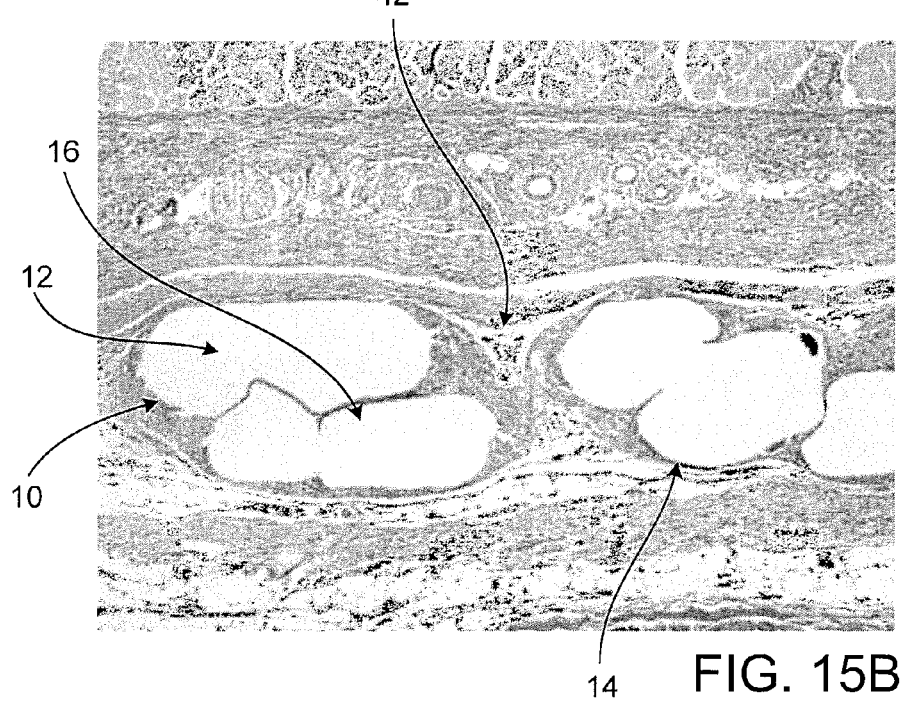
Figure 15C:
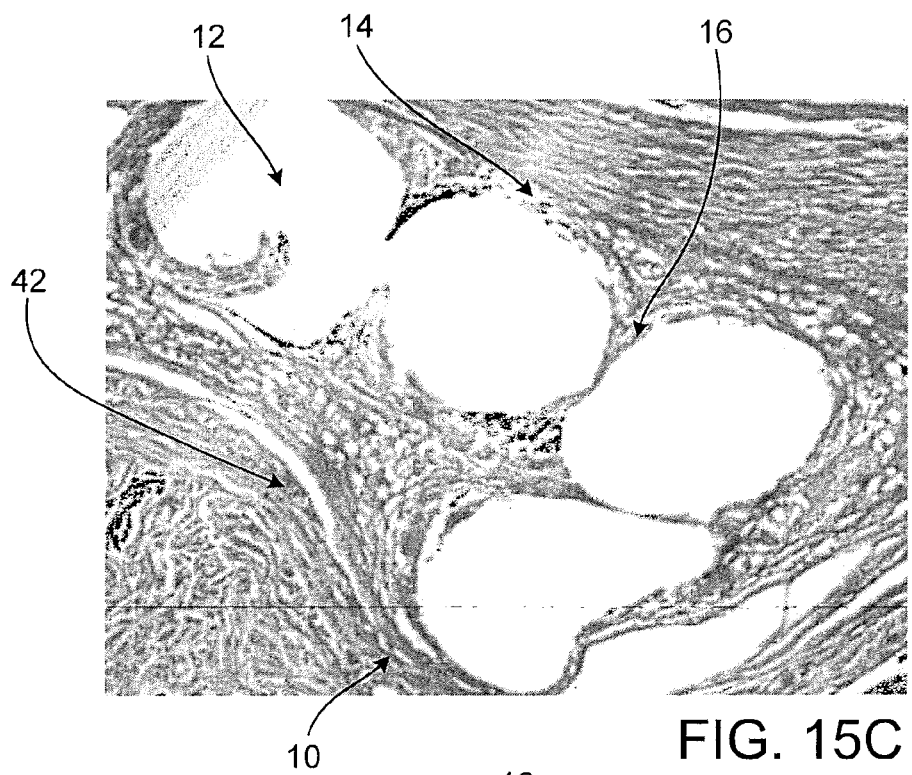
Figure 15D:
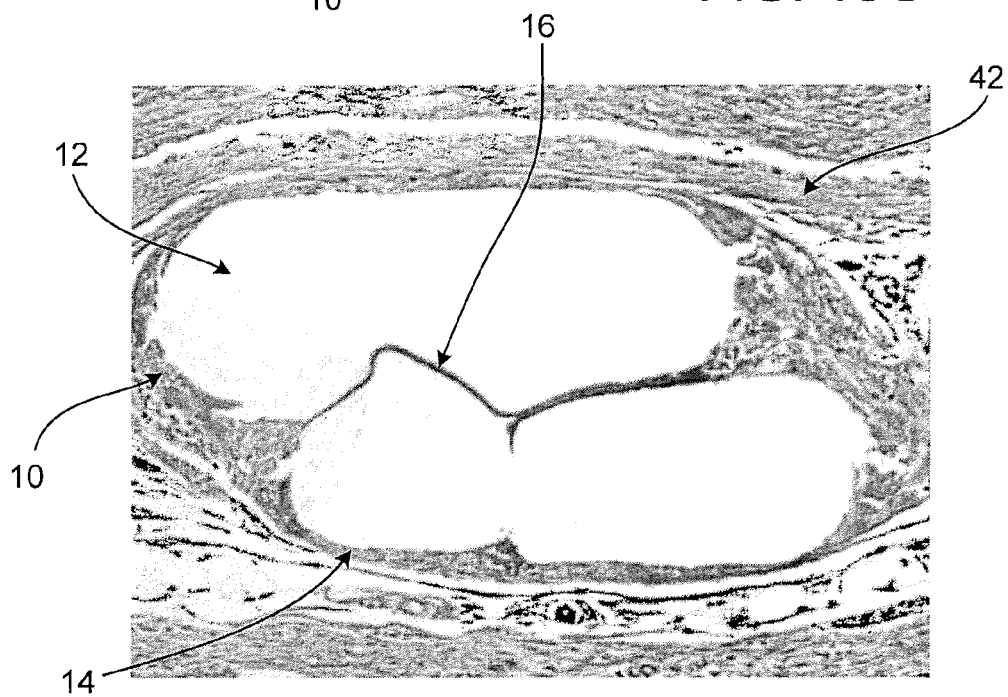

Referring to FIGS. 15A and 15C, a light micrograph of a trichrome stained 6 mil uncondensed polypropylene mesh placed subcutaneously in tissue for 28 days, at magnifications of 100× and 200×, respectively. Monofilament fibres 10 and the cross sectional areas therein 12 are visible. Collagen/scar tissue formation 42 is present around the perimeter of monofilament fibres 10 in contact with tissue 14. Referring to FIGS. 15B and 15D, a light micrograph of a trichrome stained 6 mil polypropylene mesh condensed under vacuum, heat, and a force of 75 N/cm$^2$ and placed subcutaneously in tissue for 28 days, at magnifications of 100× and 200×, respectively. Monofilament fibres 10 and the cross sectional areas therein 12 are visible. Collagen/scar tissue formation 42 is present around the perimeter of the fibres in contact with tissue 14. The thickness of the surgical mesh influences the amount of collagen/scar tissue formation 42 as the body responds to an implant by filling voids. The density and organization of the collagen/scar tissue formation is higher for thinner implants with reduced surface area.

Preliminary studies suggest the implants described herein have better properties than many existing devices. Some of the parameters described below are useful in characterizing the improvements.

Void Area Ratio=$A_v/A_f$ where $A_f$ is the area of the fibre cross sections and $A_v$ is the area of void for tissue infiltration. This ratio is particularly important at fibre intersections within the surgical mesh fabric because $A_v$ can increase in these regions when a stitch loop intersection is created. Consequently, a reduced void area is present in the condensed surgical mesh, which can lead to reduced levels of inflammation and scar tissue formation. The devices of the invention can have a Void Area Ratio of 1.50 or lower, whether calculated for the device as a whole or a portion thereof (e.g., at stitch loop intersections or in certain regions of the surgical mesh).

Surface Contact Ratio=$P_{fc}/P_f$ where $P_{fc}$ is the perimeter of fibres in contact with tissue for a cross section of the surgical mesh implant and $P_f$ is the perimeter of fibre for a cross section of the surgical mesh implant. This ratio is particularly important at fibre intersections within the surgical mesh fabric because the amount of fibre can increase in these regions when a stitch loop intersection is created. For uncondensed surgical meshes, the Surface Contact Ratio is estimated to approach 1.00 as the fibres are in direct contact only at isolated points and the majority of the fibres present are in contact with tissue. Reduced surface contact between the fibre and tissue is present in the condensed surgical mesh, which can lead to reduced levels of inflammation and scar tissue formation. The devices described herein can have a Surface Contact Ratio of 0.80 or lower whether calculated for the device as a whole or a portion thereof (e.g., at stitch loop intersections or in certain regions of the surgical mesh).

The geometry of the surface contact area of surgical mesh can also be important. The geometry of the condensation zone within condensed surgical meshes is more uniform and distributes force to tissue more evenly. The value for surface contact area under a controlled load can be measured using pressure sensitive film. The surgical mesh is placed adjacent to a pressure sensitive film (e.g., a film containing microcapsules that change colour under certain loads). Film for measuring such values is available under the trade name Prescale™ (Fujifilm). The surface contact area of the condensed surgical mesh under a controlled load can be measured in this manner. Surface contact areas for surgical meshes of a known density can be compared at different loads. Ideally, a light weight and low surface area surgical mesh with a low area density would have an increase in surface contact area with tissue under a given load to minimize irritation at isolated points. Increased surface contact area in the outer portion of low weight surgical meshes with improved void area ratios and surface contact ratios, may reduce inflammation, tissue reaction, and the erosion of the surgical mesh into adjacent tissue.

The material within the implants described herein can have uniform or non-uniform properties. For example, one or more of the physical attributes described above (e.g., the void area ratio or surface contact ratio) can vary at one or more points within the implant or along the implant's peripheral edge to improve suture or staple retention strength. For example, where the implant is a sheet of mesh, the periphery (e.g., about ⅛ to about ⅞ inches around the perimeter of the device) can remain uncondensed or be condensed to a lesser extent than the mesh within the periphery. The strength of material along the peripheral edges (e.g., the tensile strength), or at other selected points within the device, may be higher to improve the physical properties in this region so that sutures or other fixation devices do not pull out and cause failure. The material content in these regions can also be increased relative to that of the starting mesh to improve the physical properties of the device (e.g., additional material can be added to reinforce one or more points within the device). In one embodiment, attachment points such as reinforced areas or openings are created within the device (e.g., along the device's edge) for receiving sutures, staples, adhesives, and the like. The attachment points can also be used to attach separate panels to one another to create the surgical mesh implant. Accordingly, in specific embodiments, the devices can include means to facilitate coupling of an attachment element to the device (e.g., an opening for receiving an attachment element). In some instances, the device can further include all or part of an attachment element (e.g., a staple, suture, or adhesive) to facilitate attachment of the device to body tissue of a patient. The adhesive can be any biological glue or physiologically acceptable adhesive.

Alternatively, or in addition, the implant can include areas that have been adapted to increase the coefficient of friction and thereby inhibit the implant's movement in the tissue. Supporting materials, which may be included to facilitate attachment to a fastener or to generally reinforce the implant, can be shape memory materials (e.g., shape memory alloys such as Nitinol™). More generally, any of the implants can include a shape memory material such as Nitinol™ to facilitate sizing, attachment, and implantation.

The means to maintain the device in position relative to a patient's tissue (i.e., an engagement means) can be employed after implantation or deployment. Where the shape of the device alone is not sufficient to maintain its position, the engagement means can be employed after implantation or deployment. The engagement means can include one or more protrusions (e.g., a plurality of protrusions arranged in a wave-like or dimple-like pattern). Undulating elements may be in phase, with force-displacement characteristics suitable for placement and support.

The overall shape of the implants can vary tremendously and will be selected for use depending upon the size of the individual to be treated and/or the tissue to be repaired. The overall length, width, and shape of the implants can be varied and designed to support a certain area. In one embodiment, the implant includes separate panels that are positioned individually to support a tissue defect. Devices made by the methods described herein can be produced in various three-dimensional forms to facilitate placement and sizing. Generally, the implant can be configured to conform to the shape of the tissue requiring repair. For example, an implant having a curvature can be used to construct a substantially conical shape, and materials can be readily configured to extend circumferentially around a tissue. Essentially any substantially two-dimensional soft tissue implant can be thermoformed into a three-dimensional shape after condensing the surgical mesh.

In one case, a portion of the biocompatible material is movable from a delivery configuration to a deployment configuration. Preferably the delivery configuration is of a lower-profile than the deployment configuration. The device comprises means to support the portion of the biocompatible material in the deployment configuration.

Biocompatible materials useful in monofilament fibre 10 or multifilament fibre 28 can include non-absorbable polymers such as polypropylene, polyethylene, polyethylene terephthalate, polytetrafluoroethylene, polyaryletherketone, nylon, fluorinated ethylene propylene, polybutester, and silicone, or copolymers thereof (e.g., a copolymer of polypropylene and polyethylene); absorbable polymers such as polyglycolic acid (PGA), polylactic acid (PLA), polycaprolactone, polydioxanone and polyhydroxyalkanoate, or copolymers thereof (e.g., a copolymer of PGA and PLA); or tissue based materials (e.g., collagen or other biological material or tissue obtained from the patient who is to receive the implant or obtained from another person or source (e.g., an animal source)). The polymers can be of the D-isoform, the L-isoform, or a mixture of both. An example of a biocompatible fibre 10 suitable for producing the surgical mesh implant is polypropylene. Non-absorbable polymers and copolymers are not substantially resorbed by the body over time, whereas absorbable polymers degrade, to at least some appreciable extent, over time. Polymers and copolymers within commercially available surgical products, including currently available surgical meshes, are suitable for use with the present implants.

One or more layers or pieces of absorbable and non-absorbable mesh can be joined within the implant. For example, an implant can include a nonabsorbable material and an absorbable material of the same size and shape as the nonabsorbable material or a portion thereof. The absorbable material can be configured to reduce the elasticity of the implant and can be thermally attached to the nonabsorbable material.

In some embodiments, biocompatible material within the implant is shaped to distribute the stabilizing and/or supporting force exerted against tissue. The biocompatible material may comprise a surface that distributes forces against the tissue evenly.

Given the woven or knitted configuration of the mesh, the devices can facilitate tissue ingrowth and/or cellular infiltration and are porous. The pores within the devices can be arranged in regular or irregular patterns. For example, a material can include a plurality of pores of a first type (e.g., a first size and/or shape) arranged into a first pattern and of a second type (e.g., a second size or shape) arranged into a second pattern. The size of the pores can vary, and can be greater than 50 µm. In specific embodiments, one or more of the pores in the plurality has a diameter, measured along the longest axis of the pore, of about 10 to about 10,000 µm (e.g., about 10, 50, 100, 200, 500, 1,000, 2,500, 5,000, 6,000, 7,000, 8,000, or 9,000 µm). The pores can vary in shape and, either before or after condensation, may be essentially round, oval, hexagonal or diamond-shaped. One or more of the pores of the plurality may be substantially the same shape as the pores shown in FIG. 6.

The biocompatible material can have a relatively high burst and tensile strength and can have a relatively low co-efficient of friction. In another case, a portion of the base biocompatible material can have a relatively high co-efficient of friction. The devices may also comprise means to determine the magnitude and/or direction of a force (e.g., a force applied to a portion of the biocompatible material when in contact with a patient's tissue). Preferably, the device comprises means to determine the magnitude and/or direction of a force applied to the material by visual inspection. In some embodiments, the geometrical configuration of at least part of the portion of the biocompatible material can be altered in response to a change in the magnitude and/or direction of a force applied. For example, a coloured filament can be incorporated into any of the materials to create a geometry, and one may use an instrument to measure the magnitude and/or direction of a force applied to the device. The soft tissue implant may comprise areas that distribute the force transmitted to the surrounding tissue more evenly. For example, at the fibre intersections, raised fibres can create rough areas that increase the force transmitted to tissue in select areas. Similarly, the implants can include regions that have reduced cross sectional areas, which can reduce inflammation and scar tissue build up. This is especially true at fibre intersections where raised fibres can increase the cross sectional area.

The thickness of the implant can also vary and can be less than about 0.040 inches. For example, a single porous layer of mesh within the device can be less than about 0.039 inches, 0.038 inches, 0.037 inches, 0.036 inches, 0.035 inches, 0.034 inches, 0.033 inches, 0.032 inches, 0.031 inches, 0.030 inches, 0.029 inches, 0.028 inches, 0.027 inches, 0.026 inches, 0.025 inches, 0.024 inches, 0.023 inches, 0.022 inches, 0.021 inches, 0.020 inches, 0.019 inches, 0.018 inches, 0.017 inches, 0.016 inches, 0.015 inches, 0.014 inches, 0.013 inches, 0.012 inches, 0.011 inches, 0.010 inches, 0.009 inches, 0.008 inches, 0.007 inches, 0.006 inches, 0.005 inches, 0.004 inches, 0.003 inches, 0.002 inches, or about 0.001 inch. However, a given implant can include more than one layer of mesh or regions in which some portion of the mesh is covered with a second layer. For example, an implant can include a first porous biocompatible surgical mesh and a second porous biocompatible surgical mesh, the thickness of the implant being less than about 0.080 inches.

The implants can be produced by extruding a biocompatible polymer into a fibre and forming a surgical mesh implant using a textile based process. As noted, the implants are designed to engage a tissue defect and can include a bioresorbable or biodegradable material that will stay in position and support the tissue defect over a predetermined time. The implants can be produced by a number of different methods. In one embodiments, the implants are produced by extruding a first biocompatible polymer to form a fibre; forming a surgical mesh fabric from the fibre; heat setting the surgical mesh fabric; applying a nonelastic biocompatible material to the surgical mesh fabric; compressing the surgical mesh fabric to a predetermined density; reducing the thickness and roughness of the surgical mesh fabric; forming the surgical mesh fabric into a three-dimensional structure; and cutting the soft tissue implant into a predetermined shape. In this method or any other, the method may further include the steps of cleaning and/or sterilizing the implant. Once formed, the implants can be packaged for sale or distribution.

Other methods include: extruding a first biocompatible polymer to form a fibre; forming a surgical mesh fabric from the fibre; compressing the mesh fabric for a controlled period of time to a predetermined density using a combination of heat and pressure; heat setting the surgical mesh fabric; reducing the thickness and roughness of the surgical mesh fabric; forming the surgical mesh fabric into a three-dimensional structure; and cutting the soft tissue implant into a predetermined shape.

Other methods include: extruding a first biocompatible polymer to form a fibre; forming a surgical mesh fabric from the fibre; compressing the mesh fabric for a controlled period of time to a predetermined density using a combination of heat and pressure with a vacuum source; heat setting the surgical mesh fabric; compressing the surgical mesh fabric to a predetermined density; reducing the thickness and roughness of the surgical mesh fabric; forming the surgical mesh fabric into a three-dimensional structure; and cutting the soft tissue implant into a predetermined shape.

Other methods include: extruding a first biocompatible polymer to form a fibre; forming a surgical mesh fabric from the fibre; stretching the surgical mesh fabric under a predetermined load; heat setting the surgical mesh fabric; applying a nonelastic biocompatible material to the surgical mesh fabric; compressing the surgical mesh fabric to a predetermined density; reducing the thickness and roughness of the surgical mesh fabric; forming the surgical mesh fabric into a three-dimensional structure; and cutting the soft tissue implant into a predetermined shape.

Other methods include: extruding a first biocompatible polymer to form a fibre; forming a surgical mesh fabric from the fibre; heat treating the surgical mesh fabric in a manner that creates a mesh with varying pore dimensions; applying a nonelastic biocompatible material to the surgical mesh fabric; compressing the surgical mesh fabric to a predetermined density; reducing the thickness and roughness of the surgical mesh fabric; forming the surgical mesh fabric into a three-dimensional structure; and cutting the soft tissue implant into a predetermined shape.

Other methods include: extruding a first biocompatible polymer to form a fibre; forming a surgical mesh fabric from the fibre; heat setting the surgical mesh fabric; applying a nonelastic biocompatible material to the surgical mesh fabric; selectively compressing the surgical mesh fabric in certain regions to a predetermined density; reducing the thickness and roughness of the surgical mesh fabric; forming the surgical mesh fabric into a three-dimensional structure; and cutting the soft tissue implant into a predetermined shape.

Other methods include: extruding a first biocompatible polymer to form a fibre; forming a surgical mesh fabric from the fibre; heat setting the surgical mesh fabric; applying a nonelastic biocompatible material to the surgical mesh fabric; selectively compressing the surgical mesh fabric to varying degrees in certain regions to a predetermined density; reducing the thickness and roughness of the surgical mesh fabric; forming the surgical mesh fabric into a three-dimensional structure; and cutting the soft tissue implant into a predetermined shape.

A soft tissue implant can be created with a surface that has controlled texture and geometry by subjecting the mesh fabric to the above processes while in contact with a textured surface and shaped geometry at temperatures and pressures that are sufficient to permanently alter the surgical mesh implant characteristics.

Medical applications for the soft tissue implant technology described herein include but are not limited to procedures for treating stress urinary incontinence, pelvic floor prolapse, and hernia repair. The soft tissue implant can be produced or selected in a variety of shapes and sizes and from a variety of materials for a particular indication. For example, a surgeon may select a non-absorbable implant for patients that require permanent treatment with an implant having long-term durability and strength. Alternatively, the surgeon may select an absorbable soft tissue implant for patients that require temporary treatment and tissue remodelling. Generally, absorbable implants are chosen when possible to avoid the potential complications associated with a permanent implant. Consistent with the properties described herein, the surgeon can move the devices from a delivery configuration to a deployment configuration, the delivery configuration being of a lower-profile than the deployment configuration. Implants with a reduced profile can be produced and implanted in a minimally invasive fashion; as they are pliable, they can be placed or implanted through smaller surgical incisions. As the devices are also porous, they are expected to have improved optical properties, allowing the surgeon to visualize underlying tissue through the implant.

EXAMPLES

Example 1

We constructed an implant using polypropylene surgical mesh. A section of PML Prolene Mesh (Ethicon, Somerville, N.J., USA) was combined with a #2 SurgiPro™ polypropylene suture (Tyco Healthcare, North Haven, Conn., USA) to create a composite implant. The suture material was woven between the surgical mesh in 5 mm increments. The assembly was brought under vacuum to 160° C. under a force of 100 N/cm$^2$ between two layers of Apical 5 mil polyimide film using a Lauffer RLKV 40/1 vacuum lamination press. The surgical mesh had a thickness of 0.0193 inches before the pressure and heat treatment and a thickness of 0.0093 inches after the treatment. In addition, the composite assembly exhibited a lower elasticity compared to the untreated (uncondensed) surgical mesh.

Example 2

A section of SPMXXL Prolene Mesh (Ethicon, Somerville, N.J., USA) was combined with a #2 SurgiPro™ polypropylene suture (Tyco Healthcare, North Haven, Conn., USA) to create a composite implant. The suture material was woven between the surgical mesh in 5 mm increments. The assembly was brought under vacuum to 160° C. under a force of 100 N/cm$^2$ between two layer of Apical 5 mil polyimide film using a Lauffer RLKV 40/1 vacuum lamination press. The surgical mesh had a thickness of 0.0159 inches before the pressure and heat treatment and a thickness of 0.0090 inches after the treatment. In addition, the composite assembly exhibited a lower elasticity compared to the original surgical mesh.

Example 3

We constructed a knitted polypropylene surgical mesh implant using 4 mil monofilament polypropylene fibre. The fibre was produced using Marlex HGX-030-01 polypropylene homopolymer. The knitted surgical mesh had elasticity in the machine and transverse directions. A warp knit was employed to give the mesh exceptional tensile strength and to prevent runs and unravelling. A suitable mesh is produced when employing the following pattern wheel or chain drum arrangements: front guide bar, 1-0/1-2/2-3/2-1 and back guide bar, 2-3/2-1/1-0/1-2. Examples 4-10 are similar. They differ in the amount of force applied to the mesh, from 10 N/cm$^2$ to 250 N/cm$^2$, respectively.

Example 4

The surgical mesh implant disclosed in Example 3 was condensation treated. The surgical mesh implant was brought to 155° C. under 10 N/cm$^2$ with vacuum between two layers of Kapton 2 mil polyimide film using a Lauffer RLKV 40/1 vacuum lamination press.

Example 5

The surgical mesh implant disclosed in Example 3 was condensation treated. The surgical mesh implant was brought to 155° C. under 25 N/cm$^2$ with vacuum between two layers of Kapton 2 mil polyimide film using a Lauffer RLKV 40/1 vacuum lamination press.

Example 6

The surgical mesh implant disclosed in Example 3 was condensation treated. The surgical mesh implant was brought to 155° C. under 50 N/cm$^2$ with vacuum between two layers of Kapton 2 mil polyimide film using a Lauffer RLKV 40/1 vacuum lamination press.

Example 7

The surgical mesh implant disclosed in Example 3 was condensation treated. The surgical mesh implant was brought to 155° C. under 75 N/cm$^2$ with vacuum between two layers of Kapton 2 mil polyimide film using a Lauffer RLKV 40/1 vacuum lamination press.

Example 8

The surgical mesh implant disclosed in Example 3 was condensation treated. The surgical mesh implant was brought to 155° C. under 100 N/cm$^2$ with vacuum between two layers of Kapton 2 mil polyimide film using a Lauffer RLKV 40/1 vacuum lamination press.

Example 9

The surgical mesh implant disclosed in Example 3 was condensation treated. The surgical mesh implant was brought to 155° C. under 125 N/cm$^2$ with vacuum between two layers of Kapton 2 mil polyimide film using a Lauffer RLKV 40/1 vacuum lamination press.

Example 10

The surgical mesh implant disclosed in Example 3 was condensation treated. The surgical mesh implant was brought to 155° C. under 250 N/cm$^2$ with vacuum between two layers of Kapton 2 mil polyimide film using a Lauffer RLKV 40/1 vacuum lamination press.

The void area ratio of the materials described in Examples 3-10 was measured according to method described previously. The void area ratio measures the ratio of the area of the fibre cross sections and the area of void for tissue infiltration. This ratio was measured at fibre intersections within the surgical mesh fabric. A reduced void area is present in the condensed surgical mesh. It should be noted, however, that an increase in the force applied to the monofilament surgical mesh can cause damage to the fibres, which results in higher void area ratios.

Void Area Ratio

| Product | Force (N/cm$^2$) | Void Area Ratio |
| --- | --- | --- |
| Example 3 | 0 | 3.26 |
| Example 4 | 10 | 1.74 |

| Product | Force (N/cm²) | Void Area Ratio |
|---|---|---|
| Example 5 | 25 | 1.22 |
| Example 6 | 50 | 0.68 |
| Example 7 | 75 | 0.70 |
| Example 8 | 100 | 0.56 |
| Example 9 | 125 | 2.00 |
| Example 10 | 250 | 1.71 |

The surface contact ratio of the materials described in Examples 3-10 was measured according to the method described previously. The surface contact ratio measures the ratio of the perimeter of fibres in contact with tissue to the perimeter of fibres for a cross section. This ratio was measured at fibre intersections within the surgical mesh fabric. A reduced surface contact area is present in the condensed surgical mesh.

Surface Contact Ratio

| Product | Force (N/cm²) | Surface Contact Ratio |
|---|---|---|
| Example 3 | 0 | 0.88 |
| Example 4 | 10 | 0.91 |
| Example 5 | 25 | 0.69 |
| Example 6 | 50 | 0.70 |
| Example 7 | 75 | 0.52 |
| Example 8 | 100 | 0.46 |
| Example 9 | 125 | 0.62 |
| Example 10 | 250 | 0.76 |

The dimensions of the materials described in Examples 3-10, Prolene Soft™ mesh, and Mersilene™ Mesh were measured according to ASTM D5947-03 Standard Test Methods for Physical Dimensions of Solid Plastics Specimens. The thickness of the materials impacts the cross sectional area of the surgical mesh implants. In addition, the density of the material provides a measurement to determine the amount of material as it relates to cross sectional area. The density should correlate to the Void Area Ratio described above for condensed surgical mesh implants. The thickness decreases and the density increases with an increase in the condensation force applied per unit area.

Thickness

| Product | Force (N/cm²) | Thickness (cm) |
|---|---|---|
| Prolene Soft ™ Mesh | 0 | 0.040 |
| Mersilene ™ Mesh | 0 | 0.024 |
| Example 3 | 0 | 0.039 |
| Example 4 | 10 | 0.026 |
| Example 5 | 25 | 0.021 |
| Example 6 | 50 | 0.019 |
| Example 7 | 75 | 0.016 |
| Example 8 | 100 | 0.015 |
| Example 9 | 125 | 0.014 |
| Example 10 | 250 | 0.011 |

Density

| Product | Force (N/cm²) | Density (g/cm³) |
|---|---|---|
| Prolene Soft ™ Mesh | 0 | 0.081 |
| Mersilene ™ Mesh | 0 | 0.130 |
| Example 3 | 0 | 0.086 |
| Example 4 | 10 | 0.097 |
| Example 5 | 25 | 0.114 |
| Example 6 | 50 | 0.123 |
| Example 7 | 75 | 0.143 |
| Example 8 | 100 | 0.171 |
| Example 9 | 125 | 0.208 |
| Example 10 | 250 | 0.237 |

The burst strength of the materials described in Examples 3-10, Prolene Soft™ mesh, and Mersilene™ Mesh was measured according to ASTM D3787-01 Bursting Strength of Textiles (Constant Rate of Transverse). Test specimens measuring 90.0 mm wide and 90.0 mm long were loaded into a Zwick tensile test machine with a grip to grip separation of 1.0 mm and a test speed of 305 mm/min. Burst strength provides a measurement of the force required to rupture the surgical mesh implants. In addition, the ratio of density/thickness to burst strength provides a measurement of surgical mesh implant strength as it relates to the cross sectional area. The burst strength increased moderately with increase in the condensation force applied per unit area up to 125 N/cm². The sample with a condensation force of 250 N/cm² showed a decrease in burst strength.

Burst

| Product | Force (N/cm²) | Burst (Fmax N) |
|---|---|---|
| Prolene Soft ™ Mesh | 0 | 274 |
| Mersilene ™ Mesh | 0 | 129 |
| Example 3 | 0 | 194 |
| Example 4 | 10 | 222 |
| Example 5 | 25 | 210 |
| Example 6 | 50 | 225 |
| Example 7 | 75 | 223 |
| Example 8 | 100 | 209 |
| Example 9 | 125 | 227 |
| Example 10 | 250 | 195 |

Density/Burst Ratio

| Product | Force (N/cm²) | Density (g/cm³)/Burst (Fmax N) |
|---|---|---|
| Prolene Soft Mesh | 0 | 0.00030 |
| Mersilene Mesh | 0 | 0.00101 |
| Example 3 | 0 | 0.00044 |
| Example 4 | 10 | 0.00044 |
| Example 5 | 25 | 0.00054 |
| Example 6 | 50 | 0.00055 |
| Example 7 | 75 | 0.00064 |
| Example 8 | 100 | 0.00082 |
| Example 9 | 125 | 0.00092 |
| Example 10 | 250 | 0.00121 |

The suture retention of the materials described in Examples 3-10, Prolene Soft™ mesh, and Mersilene™ Mesh was measured according to ASTM D882-02 Standard Test Method for Tensile Properties of Thin Plastic Sheeting. Test specimens measuring 25.4 mm wide by 75.0 mm long were loaded into a Zwick tensile test machine with a grip to grip separation of 3.0 mm and a test speed of 500 mm/min. Materials were tested in the machine and transverse directions. Suture retention provides a measurement of the force required to disrupt the edge of the material. The suture retention strength was maintained with an increase in the condensation force applied per unit area up to 75 N/cm². The samples with a condensation force of 100 and 125 N/cm² showed a moderate decrease in suture retention strength and the samples with a condensation force of 250 N/cm² showed a more significant decrease.

Suture Machine

| Product | Force (N/cm²) | Suture Machine (Fmax N) |
|---|---|---|
| Prolene Soft ™ Mesh | 0 | 24.8 |
| Mersilene ™ Mesh | 0 | 10.0 |
| Example 3 | 0 | 21.2 |
| Example 4 | 10 | 20.0 |
| Example 5 | 25 | 22.4 |
| Example 6 | 50 | 17.4 |
| Example 7 | 75 | 20.5 |
| Example 8 | 100 | 16.2 |
| Example 9 | 125 | 15.6 |
| Example 10 | 250 | 9.3 |

Suture Transverse

| Product | Force (N/cm²) | Suture Transverse (Fmax N) |
|---|---|---|
| Prolene Soft ™ Mesh | 0 | 28.4 |
| Mersilene ™ Mesh | 0 | 11.7 |
| Example 3 | 0 | 21.4 |
| Example 4 | 10 | 20.8 |
| Example 5 | 25 | 18.8 |
| Example 6 | 50 | 20.2 |
| Example 7 | 75 | 20.0 |
| Example 8 | 100 | 20.3 |
| Example 9 | 125 | 17.3 |
| Example 10 | 250 | 12.0 |

The stiffness of the materials described in Examples 3-10, Prolene Soft™ mesh, and Mersilene™ Mesh was measured according to ASTM D4032-94 Stiffness of Fabric by the Circular Bend Procedure. Test specimens measuring 102.0 mm wide and 204.0 mm long were loaded into a Zwick tensile test machine with a grip to grip separation of 1.0 mm and a test speed of 300 mm/min. The test measures the force required to move a specimen through a circular area. It should be noted that stiffer materials may cause more irritation to surrounding tissues. The stiffness values of the condensed surgical mesh were equivalent to the uncondensed with increase in the condensation force applied per unit area up to 125 N/cm². The sample with a condensation force of 250 N/cm² showed an increase in stiffness.

Stiffness

| Product | Force (N/cm²) | Stiffness (Fmax N) |
|---|---|---|
| Prolene Soft ™ Mesh | 0 | 3.13 |
| Mersilene ™ Mesh | 0 | 0.55 |
| Example 3 | 0 | 2.35 |
| Example 4 | 10 | 1.90 |
| Example 5 | 25 | 2.35 |
| Example 6 | 50 | 2.16 |
| Example 7 | 75 | 2.03 |
| Example 8 | 100 | 2.37 |
| Example 9 | 125 | 2.34 |
| Example 10 | 250 | 2.98 |

The tensile strength of the materials described in Examples 3-10, Prolene Soft™ mesh, and Mersilene™ Mesh was measured according to ASTM D882-02 Standard Test Method for Tensile Properties of Thin Plastic Sheeting. Test specimens measuring 10.0 mm wide and 100.0 mm long were loaded into a Zwick tensile test machine with a grip to grip separation of 50.0 mm and a test speed of 500 mm/min. Materials were tested in the machine and transverse directions. Tensile strength provides a measurement of the force required to rupture the surgical mesh implants under tension. The tensile strength was maintained with an increase in the condensation force applied per unit area up to 75 N/cm². The samples with a condensation force of 100 and 125 N/cm² showed a moderate decrease in tensile strength and the samples with a condensation force of 250 N/cm² showed a more significant decrease.

Tensile Machine

| Product | Force (N/cm²) | Tensile Machine (N/cm) |
|---|---|---|
| Prolene Soft ™ Mesh | 0 | 27.75 |
| Mersilene ™ Mesh | 0 | 27.16 |
| Example 3 | 0 | 21.76 |
| Example 4 | 10 | 21.70 |
| Example 5 | 25 | 23.14 |
| Example 6 | 50 | 21.46 |
| Example 7 | 75 | 24.37 |
| Example 8 | 100 | 21.20 |
| Example 9 | 125 | 19.94 |
| Example 10 | 250 | 15.31 |

Tensile Transverse

| Product | Force (N/cm²) | Tensile Transverse (N/cm) |
|---|---|---|
| Prolene Soft ™ Mesh | 0 | 20.97 |
| Mersilene ™ Mesh | 0 | 15.04 |
| Example 3 | 0 | 17.37 |
| Example 4 | 10 | 16.69 |
| Example 5 | 25 | 17.55 |
| Example 6 | 50 | 18.02 |
| Example 7 | 75 | 16.29 |
| Example 8 | 100 | 16.41 |
| Example 9 | 125 | 15.40 |
| Example 10 | 250 | 12.39 |

Example 11

We constructed a knitted polypropylene surgical mesh implant using 4 mil monofilament polypropylene fibre. The fibre was produced using Marlex HGX-030-01 polypropylene homopolymer. A warp knit was employed to give the mesh exceptional tensile strength and to prevent runs and unravelling. A suitable mesh is produced when employing the following pattern wheel or chain drum arrangements: front guide bar, 1-0/1-2/2-3/2-1 and back guide bar, 2-3/2-1/1-0/1-2. The knitted surgical mesh had elasticity in the machine and transverse directions. The elasticity, however, was not uniform in the machine and transverse directions. The elasticity was higher in the transverse direction compared to the machine direction. To compensate for this difference, a sample measuring 33 cm in the machine direction and 45 cm in the transverse direction was stretched to 48 cm in the transverse direction while being held at 33 cm in the machine direction. The surgical mesh implant, while being held under tension, was condensation treated. The surgical mesh implant was brought to 155° C. under 75 N/cm² with vacuum between two layers of Kapton 2 mil polyimide film using a Lauffer RLKV 40/1 vacuum lamination press. The difference in elasticity between the transverse and machine directions was reduced.

A number of embodiments of the invention have been described. Nevertheless, it will be understood that various modifications may be made without departing from the spirit and scope of the invention.

The invention claimed is:

1. A soft issue implant comprising a surgical mesh formed of intertwined biocompatible monofilament fibres, wherein the mesh has a void space between adjacent fibres in the mesh, and the mesh comprises a plurality of condensation zones, each condensation zone comprising a plurality of monofilament fibre stitch loop intersections, wherein substantially all of the monofilament fibres are flattened around a circumference of the monofilament fibers on an exterior surface of the mesh at one or more of the condensation zones, wherein each flattened fibre has a cross section defining a perimeter and a cross-sectional area at the condensation zone, wherein at least one of the fibres in each condensation zone is condensed to alter the perimeter of said cross section of the fibres available for contact with tissue while maintaining the cross-sectional area of said cross section of the fibres constant, thereby providing at each condensation zone a reduced void space between the fibres of the mesh and a reduced surface area of the fibres available for contact with tissue as compared to uncondensed monofilament fibre stitch loop intersections.

2. The implant of claim 1, wherein each condensation zone comprises at least part of at least one fibre outside of a monofilament fibre stitch loop intersection, and wherein along a condensed part of a fibre, void space between the fibre and its adjacent fibre is reduced as compared to adjacent uncondensed fibres.

3. The implant of claim 2, wherein the distance between adjacent fibres in the mesh is in the range of from approximately 5 µm to approximately 500 µm.

4. The implant of claim 2, wherein along the condensed part of the fibre:

$$\frac{A_V}{A_F} \leq 1.5$$

where:
$A_V$=area of the void between adjacent fibres in the mesh available for tissue infiltration; and
$A_F$=cross-sectional area of the fibre.

5. The implant of claim 4, wherein:

$$\frac{A_V}{A_F} \leq 1.0.$$

6. The implant of claim 5, wherein:

$\frac{A_V}{A_F}$ is approximately equal to 0.6.

7. The implant of claim 1, wherein a surface area of the mesh at each condensation zone available for contact with tissue is less than the sum of total surface area of overlapping fibres.

8. The implant of claim 1, wherein the fibres comprise a polymer, a copolymer, or any combination thereof.

9. The implant of claim 8, wherein the polymer or copolymer is bioabsorbable.

10. The implant of claim 8, wherein the polymer or copolymer is non-bioabsorbable.

11. The implant of claim 1, wherein the fibres comprise polypropylene.

12. The implant of claim 1, wherein the mesh is condensed substantially uniformly.

13. The implant of claim 1, wherein the mesh comprises a condensed region and an uncondensed region.

14. The implant of claim 1, wherein the mesh comprises at least two regions that are differentially condensed.

15. The implant of claim 1, wherein the implant is configured for attachment to tissue.

16. The implant of claim 15, wherein the mesh comprises one or more attachment points.

17. The implant of claim 16, wherein the mesh is reinforced in a region of the one or more attachment points.

18. The implant of claim 16, wherein the implant is configured to couple an attachment element to the mesh.

19. The implant of claim 18, wherein the one or more attachment points comprise an attachment opening in the mesh to receive the attachment element.

20. The implant of claim 18, wherein the attachment element comprises a suture, a staple, an adhesive, or any combination thereof.

21. The implant of claim 15, wherein the mesh comprises one or more engagement formations for attachment of the mesh to tissue.

22. The implant of claim 21, wherein the one or more engagement formations comprise a protrusion.

23. The implant of claim 22, wherein the mesh comprises a plurality of protrusions configured in a wave-like or dimple like pattern.

24. The implant of claim 1, wherein at least part of the mesh is treated to increase the coefficient of friction of the mesh.

25. The implant of claim 1, wherein the mesh is configured to maintain a position of the mesh relative to tissue.

26. The implant of claim 25, wherein the mesh comprises one or more engagement formations for engaging tissue.

27. The implant of claim 1, wherein the thickness of the mesh is substantially constant across the mesh.

28. The implant of claim 1, wherein the thickness of the mesh varies across the mesh.

29. The implant of claim 1, wherein the density of the mesh varies across the mesh.

30. The implant of claim 1, wherein the mesh comprises pores of varying size across the mesh.

31. The implant of claim 1, wherein at least some of the mechanical properties of the mesh are substantially omnidirectional.

* * * * *